United States Patent [19]
Cameron et al.

[11] Patent Number: 6,153,622
[45] Date of Patent: *Nov. 28, 2000

[54] ESTROGEN AGONISTS/ANTAGONISTS

[75] Inventors: Kimberly O. Cameron, East Lyme, Conn.; Paul A. Dasilva-Jardine, Providence, R.I.; Hua Zhu Ke, Ledyard; Robert L. Rosati, Stonington, both of Conn.

[73] Assignee: Pfizer, Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/141,613

[22] Filed: Aug. 28, 1998

Related U.S. Application Data

[63] Continuation-in-part of application No. 08/849,726, filed as application No. PCT/IB95/00286, Apr. 24, 1995, which is a continuation of application No. 08/369,954, Jan. 9, 1995, Pat. No. 5,552,412.

[30] Foreign Application Priority Data

Apr. 24, 1995 [WO] WIPO ............... PCT/IB95/00286

[51] Int. Cl.⁷ ............... C07D 217/00; A61K 31/47; A61K 31/44
[52] U.S. Cl. ............... 514/307; 514/345; 546/144; 546/290
[58] Field of Search ............... 546/192, 229, 546/233, 234, 236, 237, 290, 144; 548/566, 570, 571, 575; 514/307, 345

[56] References Cited

U.S. PATENT DOCUMENTS

| | | | |
|---|---|---|---|
| 3,234,090 | 2/1966 | Huchner et al. | 548/564 |
| 3,274,213 | 9/1966 | Lednicer | 548/564 |
| 3,277,106 | 10/1966 | Bencze et al. | 548/564 |
| 3,293,263 | 12/1966 | Lednicer | 260/326.5 |
| 3,320,271 | 5/1967 | Lednicer | 260/307 |
| 3,396,169 | 8/1968 | Duncan et al. | |
| 3,483,293 | 12/1969 | Duncan et al. | |
| 3,567,737 | 3/1971 | Lednicer et al. | |
| 3,862,232 | 1/1975 | Lednicer | 260/570.7 |
| 4,133,814 | 1/1979 | Jones et al. | 260/326 |
| 4,358,593 | 11/1982 | Jones et al. | 546/202 |
| 4,380,635 | 4/1983 | Peters | 546/202 |
| 4,418,068 | 11/1983 | Jones | 424/267 |
| 5,470,854 | 11/1995 | Von Angerer et al. | 514/233.5 |
| 5,472,962 | 12/1995 | Koizumi et al. | 514/233.5 |
| 5,482,949 | 1/1996 | Black et al. | 514/324 |
| 5,484,798 | 1/1996 | Bryant et al. | 514/324 |
| 5,510,357 | 4/1996 | Palkowitz | 514/324 |
| 5,532,382 | 7/1996 | Carlson et al. | 549/57 |
| 5,552,412 | 9/1996 | Cameron et al. | 514/317 |
| 5,567,828 | 10/1996 | Dodge | 549/51 |

FOREIGN PATENT DOCUMENTS

| | | | |
|---|---|---|---|
| 0605193 | 7/1994 | European Pat. Off. | 549/60 |
| 0617030 | 9/1994 | European Pat. Off. | 549/60 |
| 9510513 | 4/1995 | WIPO | 514/307 |

OTHER PUBLICATIONS

Lednicer, Daniel, et al., J. Med. Chem. 10 78 (1967) "Mammalian Antifertility Agents. IV. Basic, 3,4–Dihydronaphthalenes and 1,2,3,4–Tetrahydro–1–naphthols".

Bencze, W.L., et al., J. Med. Chem. 10 139 (1967) "Synthetic Estrogens, Implantation Inhibitors, and Hypocholesterolemic Agents. I. Tetrahydronaphthalene Series".

Lednicer, Daniel, et al., J. Med. Chem. 12 881 (1969) "Mammalian Antifertility Agents. VII. A Novel Sequence for the Preparation of 1,2–Disubstituted 3,4–Dihydronaphthalenes".

Jones, Robert C., Acta Endocrinologica (Copenh) 1987, 114:379–382 The Effect of a Luteinizing Hormone–Releasing Hormone Antagonist on Experimental Endometriosis in the Rat.

OsteoporosisConference, CRIP No. 1812/13 Apr. 16th/20th 1993. p. 29–30.

Jones, Charles D., et al., J. Med. Chem. (1984) 27, 1057–1066 "Antiestrogens. 2. Structure–Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity".

Chemical Abstract, vol. 64, pp. 15811–15814, 1966.

Primary Examiner—Zinna Northington Davis
Attorney, Agent, or Firm—Peter C. Richardson; Gregg C. Benson; Mervin E. Brokke

[57] ABSTRACT

Compounds of this formula

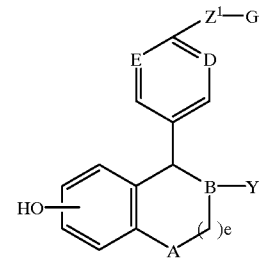

are useful for treating or preventing, obesity, breast cancer, osteoporosis, endometriosis, cardiovascular disease and prostatic disease.

25 Claims, No Drawings

ESTROGEN AGONISTS/ANTAGONISTS

This application is a continuation-in-part of application U.S. Ser. No. 08/849,726, filed Jun. 30, 1997 now allowed, which is a 371 of PCT/IB95/00286, filed Apr. 24, 1995 which is a continuation of U.S. Ser. No. 08/369,954, filed Jan. 9, 1995 which is now U.S. Pat. No. 5,552,412.

This invention relates to estrogen agonists and antagonists and their pharmaceutical uses.

BACKGROUND OF THE INVENTION

The value of naturally occurring estrogens and synthetic compositions demonstrating "estrogenic" activity has been in their medical and therapeutic uses. A traditional listing of the therapeutic applications for estrogens alone or in combination with other active agents includes: oral contraception; relief for the symptoms of menopause; prevention of threatened or habitual abortion; relief of dysmenorrhea; relief of dysfunctional uterine bleeding; an aid in ovarian development; treatment of acne; diminution of excessive growth of body hair in women (hirsutism); the prevention of cardiovascular disease; treatment of osteoporosis; treatment of prostatic carcinoma; and suppression of post-partum lactation [Goodman and Gilman, The Pharmacological Basis Of Therapeutics (Seventh Edition) Macmillan Publishing Company, 1985, pages 1421–1423]. Accordingly, there has been increasing interest in finding newly synthesized compositions and new uses for previously known compounds which are demonstrably estrogenic, this is, able to mimic the action of estrogen in estrogen responsive tissue.

From the viewpoint of pharmacologists interested in developing new drugs useful for the treatment of human diseases and specific pathological conditions, it is most important to procure compounds with some demonstrable estrogen-like function but which are devoid of proliferative side-effects. Exemplifying this latter view, osteoporosis, a disease in which bone becomes increasingly more fragile, is greatly ameliorated by the use of fully active estrogens; however, due to the recognized increased risk of uterine cancer in patients chronically treated with active estrogens, it is not clinically advisable to treat osteoporosis in intact women with fully active estrogens for prolonged periods. Accordingly estrogen agonists are the primary interest and focus.

Osteoporosis is a systemic skeletal disease, characterized by low bone mass and deterioration of bone tissue, with a consequent increase in bone fragility and susceptibility to fracture. In the U.S., the condition affects more that 25 million people and causes more than 1.3 million fractures each year, including 500,000 spine, 250,000 hip and 240,000 wrist fractures annually. These fractures cost the nation over $10 billion. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

Estrogen is often used for prevention of osteoporosis and post menopausal bone loss in women. However, estrogen stimulates the uterus and is associated with an increased risk of endometrial cancer. Although the risk of endometrial cancer is thought to be reduced by a concurrent use of a progestogen, there is still concern about possible increased risk of breast cancer with the use of estrogen.

Four classes of agents are currently approved in the U.S. for the prevention of osteoporosis in women, calcitonin, estrogen (with or without opposing progestins), bisphosphonate and roloxifene. Calcitonin has been shown to prevent postmenopausal bone loss and offer analgestic benefits. However, calcitonin's use is limited by high cost, parenteral delivery, and tachyphylaxis. A bisphosphonate has recently been approved for the treatment of osteoporosis and shows good efficacy in reducing fractures, but does not have the estrogens beneficial effects on cardiovascular system or in breast cancer. Clinically, estrogen replacement therapy in postmenopausal women is efficacious in decreasing bone turnover, reducing the incidence of vertebral and hip fractures by about 50%, decreasing the occurrence of ischemic heart disease by up to 50% and in relieving menopausal symptoms. Raloxifene was approved for osteoporosis prevention in 1997.

One third of hip fractures occurs in men. However estrogen is not suitable for use in elderly man. A new therapy for male osteoporosis is in a great medical need.

Black, et al. in EP 0605193A1 report that estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer and possibly breast cancer, causing many women to avoid this treatment. Recently suggested therapeutic regimens, which seek to lessen the cancer risk, such as administering combinations of progestogen and estrogen, cause the patient to experience unacceptable bleeding. Furthermore, combining progesterone with estrogen seems to blunt the serum cholesterol lowering effects of estrogen. The significant undesirable effects associated with estrogen therapy support the need to develop alternative therapies for hypercholesterolemia that have the desirable effect on serum LDL but do not cause undesirable effects.

There is a need for improved estrogen agonists which exert selective effects on different tissues in the body. Tamoxifen, 1-(4-β-dimethylaminoethoxyphenyl)-1,2-diphenyl-but-1-ene, is an antiestrogen which has a palliative effect on breast cancer, but is reported to have estrogenic activity in the uterus. Gill-Sharma, et al., *J. Reproduction and Fertility* (1993) 99, 395, disclose that tamoxifen at 200 and 400 mg/kg/day reduces the weights of the testes and secondary sex organs in male rats.

Recently it has been reported (Osteoporosis Conference Scrip No. 1812/13 Apr. 16/20, 1993, p. 29) that raloxifene, 6-hydroxy-2-(4-hydroxyphenyl)-3-[4-(2-piperidinoethoxy) benzoyl]benzo[b]thiophene, mimics the favorable action of estrogen on bone and lipids but, unlike estrogen, has minimal uterine stimulatory effect. (Breast Cancer Res. Treat. 10(1). 1987 p 31–36 Jordan, V. C. et al.).

Neubauer, et al., *The Prostate* 23:245 (1993) teach that raloxifene treatment of male rats produced regression of the ventral prostate.

Raloxifene and related compounds are described as antiestrogen and antiandrogenic materials which are effective in the treatment of certain mammary and prostate cancers. See U.S. Pat. No. 4,418,068 and Charles D. Jones, et al., *J. Med. Chem.* 1984, 27, 1057–1066.

Jones, et al in U.S. Pat. No. 4,133,814 describe derivatives of 2-phenyl-3-aroyl-benzothiophene and 2-phenyl-3- aroylbenzothiophene-1-oxides which are useful as antifertility agents as well as suppressing the growth of mammary tumors.

Lednicer, et al., *J. Med. Chem.*, 12, 881 (1969) described estrogen antagonists of the structure

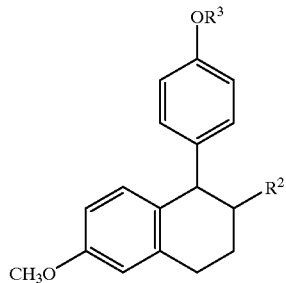

wherein $R^2$ is phenyl or cyclopentyl and $R^3$ is H,

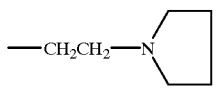

or —$CH_2CHOHCH_2OH$.

Bencze, et al., *J. Med. Chem.*, 10, 138 (1967) prepared a series of tetrahydronaphthalenes intended to achieve separation of estrogenic, antifertility and hypocholesterolemic activities. These structures are of the general formula

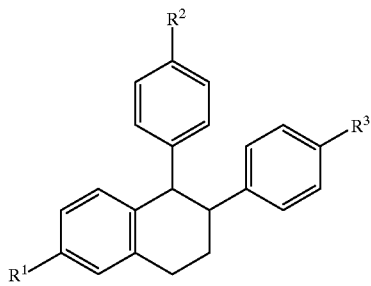

wherein $R^1$ is H or $OCH_3$; $R^2$ is H, OH, $OCH_3$, OPO $(OC_2H_5)_2$, $OCH_2CH_2N(C_2H_5)_2$, $OCH_2COOH$ or $OCH(CH_3)COOH$.

U.S. Pat. No. 3,234,090 refers to compounds which have estrogenic and antifungal properties of the formula

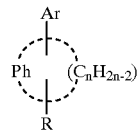

in which Ph is a 1,2-phenylene radical, Ar is a monocyclic carbocyclic aryl group substituted by tertiary amino-lower alkyl-oxy, in which tertiary amino is separated from oxy by at least two carbon atoms, R is hydrogen, an aliphatic radical, a carbocyclic aryl radical, a carbocyclic aryl-aliphatic radical, a heterocyclic aryl radical or a heterocyclic aryl aliphatic radical, the group of the formula —$(C_nH_{2n-2})$— stands for an unbranched alkylene radical having from three to five carbon atoms and carrying the groups Ar and R, salts, N-oxides, salts of N-oxides or quaternary ammonium compounds thereof, as well as procedure for the preparation of such compounds.

U.S. Pat. No. 3,277,106 refers to basic ethers with estrogenic, hypocholesterolemic and antifertility effects which are of the formula

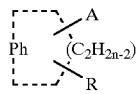

in which Ph is a 1,2-phenylene radical, Ar is a monocyclic aryl radical substituted by at least one amino-lower alkyl-oxy group in which the nitrogen atom is separated from the oxygen atom by at least two carbon atoms, R is an aryl radical, and the portion —$(C_nH_{2n-2})$— stands for lower alkylene forming with Ph a six- or seven-membered ring, two of the ring carbon atoms thereof carry the groups Ar and R, salts, N-oxides, salts of N-oxides and quaternary ammonium compounds thereof.

Lednicer, et al., in J. Med. Chem. 10, 78 (1967) and in U.S. Pat. No. 3,274,213 refer to compounds of the formula

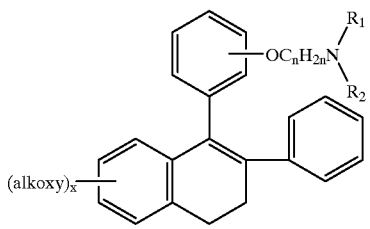

wherein $R_1$ and $R_2$ are selected from the class consisting of lower alkyl and lower alkyl linked together to form a 5 to 7 ring member saturated heterocyclic radical.

SUMMARY OF THE INVENTION

This invention provides compounds of the formula

I

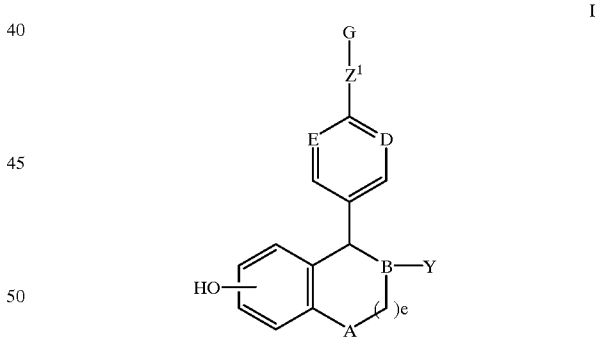

wherein:
A is selected from $CH_2$ and NR;
B, D and E are independently selected from CH and N;
Y is
(a) phenyl, optionally substituted with 1–3 substituents independently selected from $R^4$;
(b) naphthyl, optionally substituted with 1–3 substituents independently selected from $R^4$;
(c) $C_3$–$C_8$ cycloalkyl, optionally substituted with 1–2 substituents independently selected from $R^4$;
(d) $C_3$–$C_8$ cycloalkenyl, optionally substituted with 1–2 substituents independently selected from $R^4$;
(e) a five membered heterocycle containing up to two heteroatoms selected from the group consisting of —O—, —NR²— and —S(O)$_n$—, optionally substituted with 1–3 substituents independently selected from R⁴;

(f) a six membered heterocycle containing up to two heteroatoms selected from the group consisting of —O—, —NR— and —S(O)$_n$— optionally substituted with 1–3 substituents independently selected from R⁴; or (g) a bicyclic ring system consisting of a five or six membered heterocyclic ring fused to a phenyl ring, said heterocyclic ring containing up to two heteroatoms selected from the group consisting of —O—, —NR²— and —S(O)$_n$—, optionally substituted with 1–3 substituents independently selected from R⁴;

Z¹ is
(a) —(CH₂)$_p$W(CH₂)$_q$—;
(b) —O(CH₂)$_p$CR⁵R⁶—;
(c) —O(CH₂)$_p$W(CH₂)$_q$;
(d) —OCHR²CHR³—; or
(e) —SCHR²CHR³—;

G is
(a) —NR⁷R⁸;

(b)
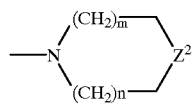

wherein n is 0, 1 or 2; m is 1, 2 or 3; Z² is —NH—, —O—, —S—, or —CH₂—; optionally fused on adjacent carbon atoms with one or two phenyl rings and, optionally independently substituted on carbon with one to three substituents and, optionally, independently on nitrogen with a chemically suitable substituent selected from R⁴; or (c) a bicyclic amine containing five to twelve carbon atoms, either bridged or fused and optionally substituted with 1–3 substituents independently selected from R⁴; or Z¹ and G in combination may be

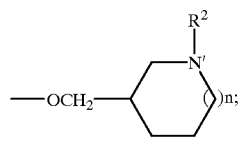

W is
(a) —CH₂—;
(b) —CH=CH—;
(c) —O—;
(d) —NR²—;
(e) —S(O)$_n$—;

(g) —CR²(OH)—;

(h) —CONR²—;
(i) —NR²CO—;

(j)
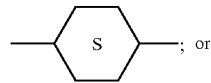; or (k) —C≡C—;

R is hydrogen or C₁–C₆ alkyl;

R² and R³ are independently
(a) hydrogen; or
(b) C₁–C₄ alkyl;

R⁴ is
(a) hydrogen;
(b) halogen;
(c) C₁–C₆ alkyl;
(d) C₁–C₄ alkoxy;
(e) C₁–C₄ acyloxy;
(f) C₁–C₄ alkylthio;
(g) C₁–C₄ alkylsulfinyl;
(h) C₁–C₄ alkylsulfonyl;
(i) hydroxy (C₁–C₄)alkyl;
(j) aryl (C₁–C₄)alkyl;
(k) —CO₂H;
(l) —CN;
(m) —CONHOR;
(n) —SO₂NHR;
(o) —NH₂;
(p) C₁–C₄ alkylamino;
(q) C₁–C₄ dialkylamino;
(r) —NHSO₂R;
(s) —NO₂;
(t) -aryl; or
(u) —OH.

R⁵ and R⁶ are independently C₁–C₈ alkyl or together form a C₃–C₁₀ carbocyclic ring;

R⁷ and R⁸ are independently
(a) phenyl;
(b) a C₃–C₁₀ carbocyclic ring, saturated or unsaturated;
(c) a C₃–C₁₀ heterocyclic ring containing up to two heteroatoms, selected from —O—, —N— and —S—;
(d) H;
(e) C₁–C₆ alkyl; or
(f) form a 3 to 8 membered nitrogen containing ring with R⁵ or R⁶

R⁷ and R⁸ in either linear or ring form may optionally be substituted with up to three substituents independently selected from C₁–C₆ alkyl, halogen, alkoxy, hydroxy and carboxy;

a ring formed by R⁷ and R⁸ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, and quaternary ammonium salts thereof.

Preferred compounds of the invention are of the formula:

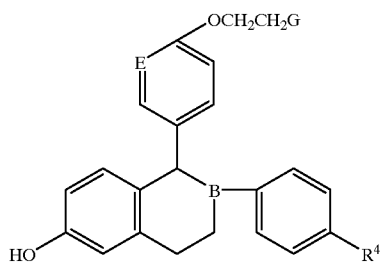

wherein G is

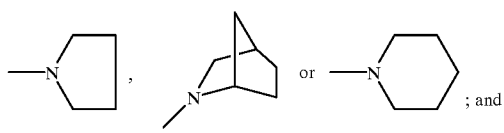

$R^4$ is H, OH, F, or Cl; and B and E are independently selected from CH and N.

Especially preferred compounds are:

Cis-6-(4-fluoro-phenyl)-5-[4-(2-piperidin-1-yl-ethoxy)-phenyl]-5,6,7,8-tetrahydro-naphthalen-2-ol;

(−)-Cis-6-phenyl-5-[4-(2-pyrrolidin-1-yl-ethoxy)-phenyl]-5,6,7,8-tetrahydro-naphthalen-2-ol;

Cis-6-phenyl-5-[4-(2-pyrrolidin-1-yl-ethoxy)-phenyl]-5,6,7,8-tetrahydro-naphthalen-2-ol;

Cis-1-[6'-pyrrolodinoethoxy-3'-pyridyl]-2-phenyl-6-hydroxy-1,2,3,4-tetrahydrohaphthalene;

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydro-naphthalen-2-ol; and 1-(4'-Pyrrolidinolethoxyphenyl)-2-phenyl-6-hydroxy-1,2,3,4-tetrahydroisoquinoline.

In another aspect this invention provides methods of treating or preventing a condition selected from breast cancer, osteoporosis, endometriosis and cardiovascular disease and hypercholesterolemia in male or female mammals and benign prostatic hypertrophy and prostatic carcinomas in male mammals which comprises administering to said mammal an amount of a compound of formula I and preferably a preferred compound of formula I compounds as described above which is effective in treating or preventing said condition.

In another aspect this invention provides a method of treating or preventing obesity in mammals which comprises administering to said mammal an amount of a compound of formula I and preferably a preferred compound of formula I as described above which is effective in treating or preventing obesity.

In yet another aspect this invention provides a pharmaceutical composition for treating or preventing breast cancer, osteoporosis, obesity, cardiovascular disease, hypercholesterolemia, endometriosis and prostatic disease comprising a compound of formula I and a pharmaceutically acceptable carrier.

This invention provides an estrogen agonist which inhibits bone resorption and bone turnover, prevents bone loss, preserves bone strength, and decreases serum cholesterol without causing prostate hypertrophy in adult male ORX rats, a model of male osteoporosis.

In another aspect, this invention provides intermediate compounds useful in preparing compounds of Formula I. These are 1-{2-[4-(6-Methoxy-3,4-dihydronaphthalen-1-yl)phenoxy]ethyl}pyrrolidine and 1-{2-[4-(2-Bromo-6-methoxy-3,4-dihydronaphthalen-1-yl)phenoxy]ethyl}pyrrolidine.

DETAILED DESCRIPTION OF THE INVENTION

The terms $C_1$–$C_3$ chloroalkyl and $C_1$–$C_3$ fluoroalkyl include methyl, ethyl, propyl and isopropyl substituted to any desired degree with chlorine or fluorine atoms, from one atom to full substitution. The term $C_5$–$C_7$ cycloalkyl includes cyclopentyl, cyclohexyl and cycloheptyl.

Halo means chloro, bromo, iodo and fluoro. Aryl (Ar) includes phenyl and naphthyl optionally substituted with one to three substituents independently selected from $R^4$ as defined above. DTT means dithiothreitol. DMSO means dimethyl sulfoxide. EDTA means ethylene diamine tetra acetic acid.

Estrogen agonists are herein defined as chemical compounds capable of binding to the estrogen receptor sites in mammalian tissue, and mimicking the actions of estrogen in one or more tissues.

Estrogen antagonists are herein defined as chemical compounds capable of binding to the estrogen receptor sites in mammalian tissue, and blocking the actions of estrogen in one or more tissues.

One of ordinary skill will recognize that certain substituents listed in this invention will be chemically incompatible with one another or with the heteroatoms in the compounds, and will avoid these incompatibilities in selecting compounds of this invention. Likewise certain functional groups may require protecting groups during synthetic procedures which the chemist of ordinary skill will recognize.

The chemist of ordinary skill will recognize that certain compounds of this invention will contain atoms which may be in a particular optical or geometric configuration. All such isomers are included in this invention; exemplary levorotatory isomers in the cis configuration are preferred. Likewise, the chemist will recognize that various pharmaceutically acceptable esters and salts may be prepared from certain compounds of this invention. All of such esters and salts are included in this invention.

As used in this application, prostatic disease means benign prostatic hyperplasia or prostatic carcinoma.

The remedies for the prostatic diseases, breast cancer, obesity, cardiovascular disease, hypercholesterolemia and osteoporosis of this invention comprise, as active ingredient, a compound of formula I or a salt or ester thereof. The pharmaceutically acceptable salts of the compounds of formula I are salts of non-toxic type commonly used, such as salts with organic acids (e.g., formic, acetic, trifluoroacetic, citric, maleic, tartaric, methanesulfonic, benzenesulfonic or toluenesulfonic acids), inorganic acids (e.g. hydrochloric, hydrobromic, sulfuric or phosphoric acids), and amino acids (e.g., aspartic or glutamic acids). These salts may be prepared by the methods known to chemists of ordinary skill.

The remedies for prostatic diseases, breast cancer, obesity, cardiovascular disease, hypercholesterolemia and osteoporosis of this invention may be administered to animals including humans orally or parenterally in the conventional form of preparations, such as capsules, microcapsules, tablets, granules, powder, troches, pills, suppositories, injections, suspensions and syrups.

The remedies for prostatic diseases, breast cancer, obesity, cardiovascular disease, hypercholesterolemia and osteoporosis of this invention may be administered transdermally through the use of a transdermal patch containing the active compound and a carrier that is inert to the active compound, is non toxic to the skin, and allows delivey of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane coveting a reservior containing the active ingredient with or without a carrier, or a matrix containing the active ingredient. Other occlusive devices are known in the literature.

The remedies for prostatic diseases, breast cancer, obesity, cardiovascular disease, hypercholesterolemia and osteoporosis of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silici acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutica effect; for example, about 0.1 mg to 50 mg in unit dosage for both oral and parenteral administration.

The active ingredient may be usually administered once to four times a day with a unit dosage of 0.1 mg to 50 mg in human patients, but the above dosage may be properly varied depending on the age, body weight and medical condition of the patient and the type of administration. A preferred dose is 0.25 mg to 25 mg in human patients. One dose per day is preferred.

Compounds of this invention are readily prepared by the reactions illustrated in the schemes below.

Certain compounds of formula I are conveniently prepared from an unsaturated intermediate

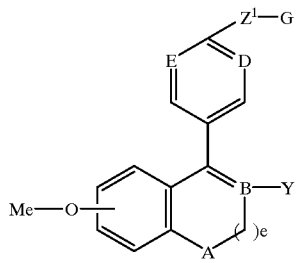

II by hydrogenation with a noble metal catalyst in a reaction inert solvent. Pressure and temperatures are not critical and hydrogenation is normally accomplished in a few hours at room temperatures at 20–80 psi hydrogen pressure.

The hydrogenated product is isolated, purified if desired, and the ether group is cleaved with an acidic catalyst in a reaction inert solvent at a temperature between 0° C. to 100° C. depending on the acidic catalyst used. Hydrogen bromide at elevated temperatures, boron tribromide and aluminum chloride at 0° C. to ambient temperature have been found to be effective for this reaction.

The product, Formula I is isolated and purified by standard procedures.

Intermediates of Formula II where A is $CH_2$, and B, D and E are CH are described in U.S. Pat. No. 3,274,213; J. Med. Chem 10, 78 (1967); J. Med. Chem 10, 138 (1967); and J. Med. Chem. 12, 881 (1969), the disclosures of which are herein incorporated by reference. They can also be prepared by procedures described below.

The preparation of the compounds of Formula I where e=1, A=$CH_2$, $Z^1$=$OCH_2CH_2$, G=cycloalkylamine, B=CH is shown in Scheme 1. Compounds 1–2, where D and E are CH are made by alkylation of 4-bromophenol with the corresponding N-chloroethylamine using potassium carbonate as base in a polar aprotic solvent like dimethylformamide at elevated temperatures. A preferred temperature is 100° C. Compounds 1-2 where D or E or both are N are synthesized using a nucleophilic displacement reaction performed on dibromides (1-1) using hydroxy ethyl cycloalkylamines under phase transfer conditions to afford bromo amines (1-2). Synthesis, 77, 573 (1980). Following halogen metal exchange using n-butyllithium or magnesium metal, bromo amines (1-2) yield the corresponding lithium or magnesium reagents which are allowed to react at low temperature in the presence of cesium chloride preferably (without cesium chloride the reaction also proceeds) with 6-methoxy-1-tetralone to afford either carbinols (1-3) or styrenes (1-4) after acidic workup. Treatment of either carbinols (1-3) or styrenes (1-4) with a brominating agent such as pyridinium bromide perbromide affords bromo styrenes (1-5). Aryl or heteroaryl zinc chlorides or aryl or heteroaryl boronic acids react with bromides (1-5) in the presence of a palladium metal catalyst like tetrakis triphenyl phosphine palladium (0) to yield diaryl styrenes (1-6). [Pure & Applied Chem. 63, 419, (1991) and Bull. Chem. Soc. Jpn. 61, 3008–3010, (1988)]. To prepare the preferred compounds the substituted phenyl zinc chlorides or substituted phenylboronic acids are used in this reaction. The aryl zinc chlorides are prepared by quench of the corresponding lithium reagent with anhydrous zinc chloride. The aryl boronic acids, that are not commercially available, are prepared by quenching the corresponding aryl lithium reagent with trialkyl borate, preferably the trimethyl or triisopropyl borate, followed by aqueous acid workup. Acta Chemica Scan. 47, 221–230 (1993). The lithium reagents that are not commercially available are prepared by halogen metal exchange of the corresponding bromide or halide with n-butyl or t-butyllithium. Alternately, the lithium reagent is prepared by heteroatom facilitated lithiations as described in Organic Reactions, Volume 27, Chapter 1. Catalytic hydrogenation of 1–6 in the presence of palladium hydroxide on charcoal, for example, affords the corresponding dihydro methoxy intermediates which were subsequently demethylated using boron tribromide at 0° C. in methylene chloride or 48% hydrogen bromide in acetic acid at 80–100° C. to afford target structures (1-7). These compounds are racemic and can be resolved into the enantiomers via high pressure liquid chromatography using a column with a chiral stationary phase like the Chiralcel OD columns. Alternately optical resolution can be carried out by recrystallization of the diastereomeric salts formed with optically pure acids like 1,1'-binapthyl-2,2'-diyl hydrogen phosphate (see Example 8).

The cis compounds (1-7) can be isomerized to the trans compounds on treatment with base (see Example 2).

When D and/or E is nitrogen the intermediates (Formula II) and compounds of Formula I may be prepared from the corresponding dihalopyridines or pyrimidines as illustrated in Scheme 1 and as fully described for 6-phenyl-5-[6-(2-pyrrolidin-1-yl-ethoxy) pyridin-3-yl]-5,6,7,8-tetrahydronaphthalen-2-ol in Example 6.

The methyl ether of the compound of Formula I where e=1, A=CH$_2$, Z$^1$=OCH$_2$CH$_2$, G=pyrrolidine, D,E, B=CH, Y=Ph can also be conveniently prepared by a first step of hydrogenation of nafoxidine (Upjohn & Co., 700 Portage Road, Kalamazoo, Mich. 49001) in a reaction inert solvent in the presence of a nobel metal catalyst. Pressure and temperature are not critical; the reaction is conveniently run in ethanol at room temperature for approximately 20 hours at 50 psi.

The second step is cleavage of the methoxy group which is accomplished conveniently at room temperature with an acidic catalyst such as boron tribromide in a reaction inert solvent or at 80–100° C. with hydrogen bromide in acetic acid. The product is then isolated by conventional methods and converted to an acid salt if desired.

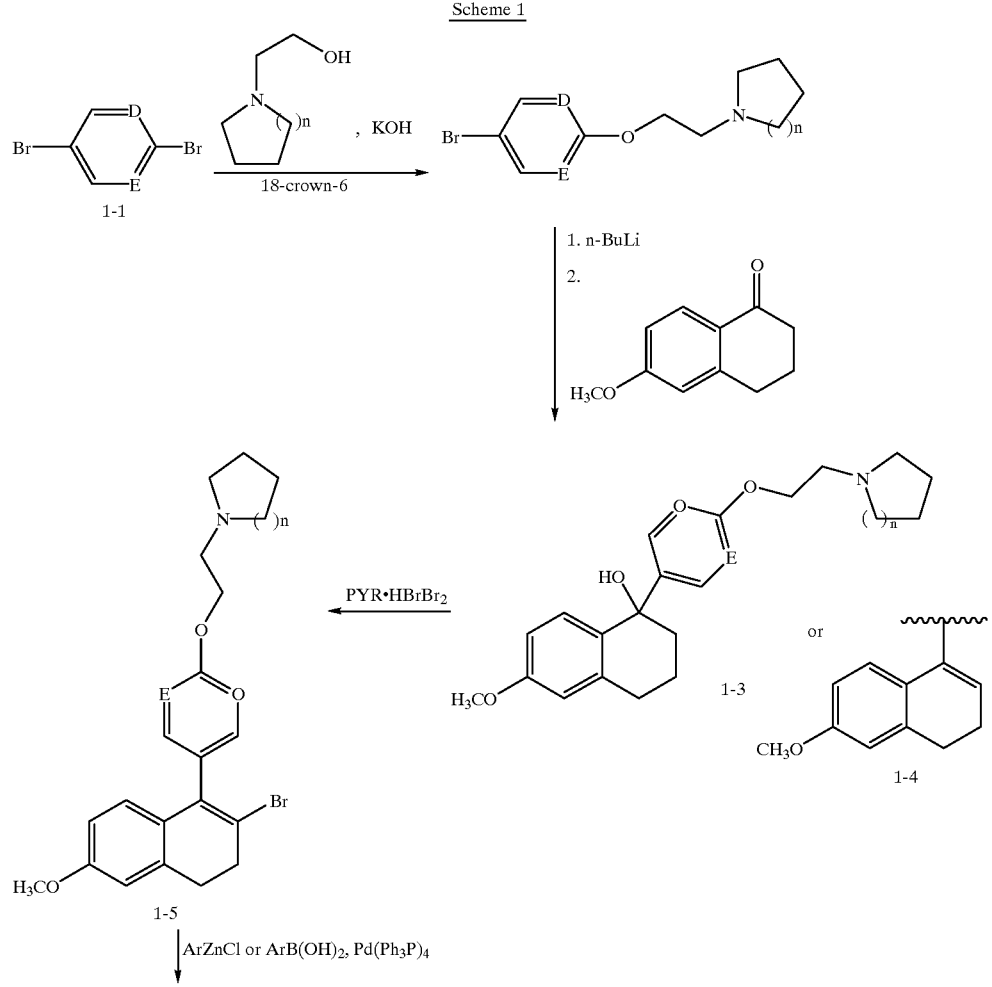

Scheme 1

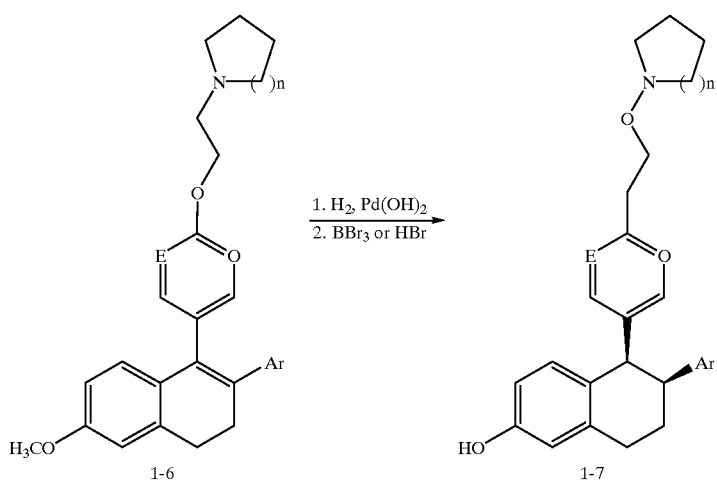

Compounds of formula I wherein B is nitrogen are prepared by the procedures illustrated in Scheme 2 and 3 and Examples 3–5 and 10–12.

The synthesis of compounds of Formula I where B=N is shown in Scheme 2. Aryl acid chlorides (2-1) on treatment with primary amines afford aryl secondary amides (2-2), which are reduced with lithium aluminum hydride in ethereal solvents to yield secondary amines (2-3). Subsequent acylation of (2-3) with aroyl acid chlorides leads to tertiary amides (2-4), which are cyclized in hot phosphorus oxychloride to yield dihydro isoquinolinium salts (2-5). Reduction with sodium borohydride to alkoxytetrahydro isoquinolines; followed by boron tribromide demethylation in methylene chloride affords the target structures.

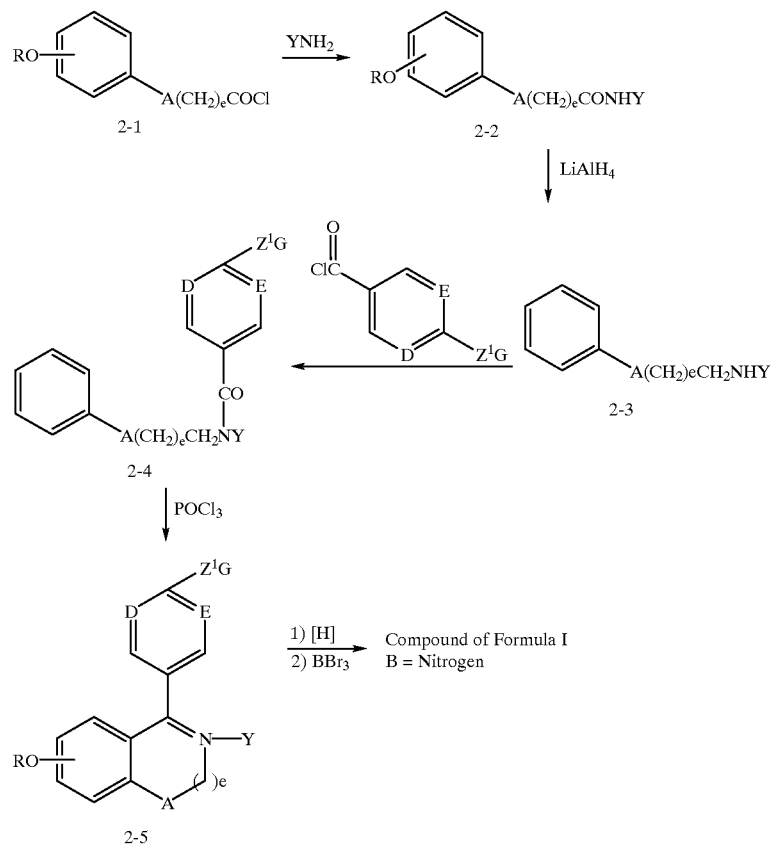

The synthesis of the compounds of Formula I where B=N is also described below in Scheme 3. Secondary amines (3-1) on acylation with benzyloxyaroyl chlorides (3-2) afford tertiary amides (3-3) which on cyclization with hot phosphorous oxychloride yield dihydro isoquinoline salts (3-4). Sodium borohydride reduction of (3-4) followed by debenzylation with aqueous hydrochloric acid affords isoquinolines (3-5), which are alkylated with the appropriately functionalized chlorides and demethylated with boron tribromide to yield the desired target structures.

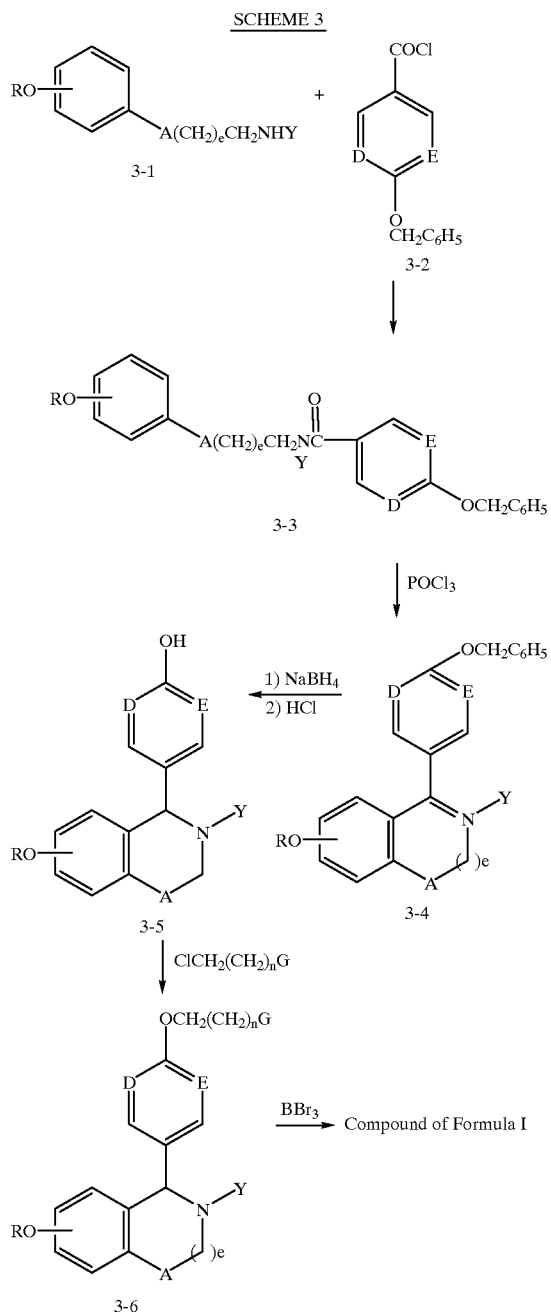

The compounds of this invention are valuable estrogen agonists and pharmaceutical agents or intermediates thereto. Those which are estrogen agonists are useful for oral contraception; relief for the symptoms of menopause; prevention of threatened or habitual abortion; relief of dysmenorrhea; relief of dysfunctional uterine bleeding; relief of endometriosis; an aid in ovarian development; treatment of acne; diminution of excessive growth of body hair in women (hirsutism); the prevention and treatment of cardiovascular disease; prevention and treatment of atherosclerosis; prevention and treatment of osteoporosis; treatment of benign prostatic hyperplasia and prostatic carcinoma obesity; and suppression of post-partum lactation. These agents also have a beneficial effect on plasma lipid levels and as such are useful in treating and preventing hypercholesterolemia.

While the compounds of this invention are estrogen agonists in bone, they are also antiestrogens in breast tissue and as such would be useful in the treatment and prevention of breast cancer.

Control and Prevention of Endometriosis

The protocol for surgically inducing endometriosis is identical to that described by Jones, *Acta Endocrinol* (Copenh) 106:282–8. Adult Charles River Sprague-Dawley CD® female rats (200–240 g) are used. An oblique ventral incision is made through the skin and musculature of the body wall. A segment of the right uterine horn is excised, the myometrium is separated from the endometrium, and the segment is cut longitudinally. A 5×5 mm section of the endometrium, with the epithelial lining apposed to the body wall, is sutured at its four corners to the muscle using polyester braid (Ethiflex, 7-0®). The criterion of a viable graft is the accumulation of fluid similar to that which occurs in the uterus as a result of estrogen stimulation.

Three weeks after transplantation of the endometrial tissue (+3 weeks) the animals are laparotomized, the volume of the explant (length×width×height) in mm was measured with calipers, and treatment is begun. The animals are injected sc for 3 weeks with 10 to 1000 μg/kg/day of a compound of Formula I. Animals bearing endometrial explants are injected sc with 0.1 ml/day of corn oil for 3 weeks served as controls. At the end of 3 week treatment period (+6 weeks), the animals are laparotomized and the volume of the explant determined. Eight weeks after cessation of treatment (+14 weeks) the animals are sacrificed; the explant are measured again. Statistical analysis of the explant volume is by an analysis of variance.

Effect on Prostate Weight

Male Sprague-Dawley rats, three months of age are administered by subcutaneous injection either vehicle (10% ethanol in water), estradiol (30 μg/kg), testosterone (1 mg/kg) or a compound of formula I daily for 14 days (n=6/group). After 14 days, the animals are sacrificed, the prostate is removed, and the wet prostate weight is determined. Mean weight is determined and statistical significance (p<0.05) is determined compared to the vehicle-treated group using Student's t-test.

The compounds of formula I significantly (P<0.05) decrease prostate weight compared to vehicle. Testosterone has no effect, while estrogen at 30 μg/kg significantly reduces prostate weight.

Female Bone Mineral Density

Bone mineral density, a measure of bone mineral content, accounts for greater than 80% of a bone's strength. Loss of bone mineral density with age and/or disease reduces a bone's strength and renders it more prone to fracture. Bone mineral content is accurately measured in people and animals by dual x-ray absorptiometry (DEXA) such that changes as little as 1% can be quantified. We have utilized DEXA to evaluate changes in bone mineral density due to estrogen deficiency following ovariectomy (surgical removal of ovaries) and treatment with vehicle, estradiol (E2), keoxifen (raloxifen), or other estrogen agonists. The purpose of these studies is to evaluate the ability of the compounds of this invention to prevent estrogen deficiency bone loss as measured by DEXA.

Female (S-D) rats 4–6 months of age undergo bilateral ovariectomy or sham surgery and allowed to recover from anesthesia. Rats are treated by s.c. injection or oral gavage with various doses (1–1000 μg/kg/day, for example) of compound of Formula I daily for 28 days. All compounds are weighed and dissolved in 10% ethanol in sterile saline. After 28 days the rats are killed and femora removed and defleshed. The femoral are positioned on a Hologic QDR1000W (Hologic, Inc. Waltham, Mass.) and bone mineral density is determined in the distal portion of the femur at a site from 1 cm to 2 cm from the distal end of the femur using the high resolution software supplied by Hologic. Bone mineral density is determined by dividing the bone mineral content by the bone area of the distal femur. Each group contains at least 6 animals. Mean bone mineral density is obtained for each animal and statistical differences (p<0.05) from the vehicle-treated ovariectomy and sham-operated group were determined by t test.

Male Osteoporosis

A new therapy for male osteoporosis is a great medical need. It has been demonstrated that selective estrogen receptor modulators (SERMs) can prevent bone loss in female ovariectomized (OVX) rats and in postmenopausal women. However their effects in adult orchidectomized (ORX) rats, a model of male osteoporosis, are not known. (−)Cis-6-phenyl-5-[4-(2-pyrrolidin-1-yl-ethoxy)phenyl]-5,6,7,8-tetrahydronaphthalen-2-ol is a highly potent tissue selective estrogen receptor modulator, which prevents bone loss in OVX rats with an oral $ED_{50}$ of approximately 1 μg/kg/day, combined with favorable effects on total serum cholesterol and prostate weight and histology in adult ORX rats.

Fifty Sprague-Dawley male rats were sham-operated (n=10) or ORX (n=40) at 10 months of age. Ten rats were autopsied on day 0 as basal controls. ORX rats were treated (daily p.o.) with either vehicle (10% ethanol in water) or (−)Cis-6-phenyl-5-[4-(2-pyrrolidin-1-yl-ethoxy)phenyl]-5,6,7,8-tetrahydronaphthalen-2-ol at 1, 10, or 100 μg/kg/day for 60 days. There were 10 rats per each subgroup, all rats were given subcutaneous injections with 10 mg/kg of calcein (Sigma Chemical Co., St. Louis, Mo.) on 13 and 3 days before autopsy.

1) Total serum cholesterol: Total serum cholesterol was determined using a high performance cholesterol colorometric assay (Boehringer Mannheim Biochemicals, Indianapolis, Ind.).

2) Prostate weight: The prostate weight was determined immediately at autopsy.

3) Femoral Bone Mineral Measurements: The right femur from each rat was removed at autopsy and scanned using dual energy x-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution was 0.0254×0.0127 cm and scan speed is 7.25 mim/second. The femoral scan images were analyzed and bone area, bone mineral content (BMC), and bone mineral density (BMD) of whole femora (WF), distal femoral metaphyses (DFM), femoral shaft (FS) were determined according to the method described in H. Z. Ke et al., Droloxifene, a New Estrogen Antagonist/Agonist, Prevents Bone Loss in Ovariectomized Rats. ENDOCRINOLOGY 136;2435–2441, 1995.

4) Third Lumbar Vertebral Body (LV3) Histomorphometry: The LV3 was removed at autopsy, dissected free of muscle, fixed in 70% ethanol, dehydrated in graded concentrations of ethanol, defatted in acetone, then embedded in methyl methacrylate (Eastman Organic Chemicals, Rochester, N.Y.). Longitudinal sections of LV3 at 4 and 10 μm thickness were cut using Reichert-Jung Polycut S microtome. One 4 μm and one 10 μm sections from each rat will be used for cancellous bone histomorphometry. The 4 μm sections were stained with modified Masson's Trichrome stain while the 10 μm sections remained unstained.

A Bioquant OS/2 histomorphometry system (R&M Biometrics, Inc., Nashville, Tenn.) was used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region need to be omitted in order to restrict measurements to the secondary spongiosa. The 4 μm sections will be used to determine indices related to bone volume, bone structure, and bone resorption, while the 10 μm sections will be used to determine indices related to bone formation and bone turnover.

(A). Measurements and Calculations Related to Trabecular Bone Volume and Structure 1. Total metaphyseal area (TV, $mm^2$): metaphyseal area between 1.2 and 3.6 mm distal to the growth plate-epiphyseal junction.

2. Trabecular bone area (BV, $mm^2$): total area of trabeculae within TV.

3. Trabecular bone perimeter (BS, mm): the length of total perimeter of trabeculae.

4. Trabecular bone volume (BV/TV,%): BV/TV×100.

5. Trabecular bone number (TBN,#/mm): 1.199/2×BS/TV.

6. Trabecular bone thickness (TBT, μm): (2000/1.199)×(BV/BS).

7. Trabecular bone separation (TBS, μm): (2000×1.199)×(TV−BV).

(B). Measurements and Calculations Related to Bone Resorption

1. Osteoclast number (OCN, #): total number of osteoclast within total metaphyseal area.

2. Osteoclast perimeter (OCP, mm): length of trabecular perimeter covered by osteoclast.

3. Osteoclast number/mm (OCN/mm, #/mm): OCN/BS.

4. Percent osteoclast perimeter (% OCP,%): OCP/BS×100.

(C). Measurements and Calculations Related to Bone Formation and Turnover

1. Single-calcein labeled perimeter (SLS, mm): total length of trabecular perimeter labeled with one calcein label.

2. Double-calcein labeled perimeter (DLS, mm): total length of trabecular perimeter labeled with two calcein labels.

3. Inter-labeled width (ILW, μm): average distance between two calcein labels.

4. Percent mineralizing perimeter (PMS,%):(SLS/2+DLS)/BS×100.

5. Mineral apposition rate (MAR, μm/day): ILW/label interval.

6. Bone formation rate/surface ref. (BFR/BS, $μm^2/d/μm$): (SLS/2+DLS)×MAR/BS.

7. Bone turnover rate (BTR, %/y): (SLS/2+DLS)×MAR/BV×100. 5) Compression test of fifth lumbar vertebral body (FIG. 1B). Using a Material Testing System (Model 810, MTS Systems Corp., Minneapolis, Minn.), mechanical testings were performed on the fifth lumbar vertebral body (LV5). The load displacement curve was obtained from each test. A compression test was used to determine the mechanical properties of LV5, as described by Mosekilde et al. (Mosekilde, L., Danielsen, C. C., Gasser, J. The effect on vertebral bone mass and strength of long term treatment with antiresorptive agents, human PTH (1-38), and combination therapy, assessed in aged ovariectomized rats. Endocrinol 1994; 134:2126–2134). LV5 (with the two epiphyseal ends, posterior pedicle arch and spinous process removed) was compressed to failure at a displacement rate of 0.1 mm/second using a 2.5 kN load cell (MTS model 661, 14A-03). The maximal load and stiffness were calculated from the load-displacement curve.

Age-related decreases in DFBMD (−9%), trabecular bone volume (TBV, −13%) were found in sham controls when compared to basal controls. ORX induced significant increases in total serum cholesterol (+31%), bone resorption surface (+48%) and activation frequency (bone turnover, +103%), and significant decreases in distal femoral bone mineral density (DFBMD, −14%), TBV (−23%), maximal load (−17%) when compared to basal controls. (−)Cis-6-phenyl-5-[4-(2-pyrrolidin-1-yl-ethoxy)phenyl]-5,6,7,8-tetrahydronaphthalen-2-ol dose-dependently decreased body weight and total serum cholesterol when compared to both sham and ORX controls. Compared to ORX controls, (−)Cis-6-phenyl-5-[4-(2-pyrrolidin-1-yl-ethoxy)phenyl]-5,6,7,8-tetrahydronaphthalen-2-ol at 10 or 100 µg/kg/day significantly decreased bone resorption and bone turnover and completely prevented age-related and ORX-induced decreases in DFBMD, TBV, and maximal load. (−)Cis-6-phenyl-5-[4-(2-pyrrolidin-1-yl-ethoxy)phenyl]-5,6,7,8-tetrahydronaphthalen-2-ol at 10 and 100 µg/kg/d significantly decreased total serum cholesterol by 46% and 68% in ORX rats, while no effect was found in prostate weight and histology parameters when compared to ORX controls.

|  | Maximal Load of LV$_5$ (N) | Activation Frequency (#/year) |
| --- | --- | --- |
| Basal | 362 ± 24 | 1.67 ± 0.21 |
| Sham | 340 ± 33 | 1.26 ± 0.27 |
| ORX | 302 ± 15* | 2.56 ± 0.35* |
| 1 mg | 337 ± 36 | 2.67 ± 0.34* |
| 10 µg | 393 ± 27# | 2.06 ± 0.28 |
| 100 µg | 393 ± 25# | 0.93 ± 0.08# |

*: $p < 0.05$ vs. Sham; #: $p < 0.05$ vs. ORX

These data showed that (−)Cis-6-phenyl-5-[4-(2-pyrrolidin-1-yl-ethoxy)phenyl]-5,6,7,8-tetrahydronaphthalen-2-ol a selective estrogen receptor modulator, inhibits bone resorption and bone turnover, prevents bone loss, preserves bone strength, and decreases serum cholesterol without causing prostate hypertrophy in adult ORX rats, a model of male osteoporosis.

In Vitro Estrogen Receptor Binding Assay

An in vitro estrogen receptor binding assay, which measures the ability of the compounds of the present invention to displace [3H]-estradiol from human estrogen receptor obtained by recombinant methods in yeast, is used to determine the estrogen receptor binding affinity of the compounds of this invention. The materials used in this assay are: (1) Assay buffer, TD-0.3 (containing 10 nM Tris, pH 7.6, 0.3 M potassium chloride and 5 mM DTT, pH 7.6); (2) The radioligand used is [3H]-estradiol obtained from New England Nuclear; (3) the cold ligand used is estradiol obtained from Sigma (4) recombinant human estrogen receptor, hER.

A solution of the compound being tested is prepared in TD-0.3 with 4% DMSO and 16% ethanol. The tritiated estradiol is dissolved in TD-0.3 such that the final concentration in the assay was 5 nM. The hER is also diluted with TD-0.3 such that 4–10 µg of total protein was in each assay well. Using microtitre plates, each incubate received 50 ul of cold estradiol (nonspecific binding) or the compound solution, 20 uL of the tritiated estradiol and 30 ul of hER solutions. Each plate contains in triplicate total binding and varying concentrations of the compound. The plates are incubated overnight at 4° C. The binding reaction is then terminated by the addition and mixing of 100 mL of 3% hydroxylapatite in 10 mM tris, pH 7.6 and incubation for 15 minutes at 4° C. The mixtures are centrifuged and the pellet washed four times with 1% Triton-X100 in 10 mM Tris, pH 7.6. The hydroxylapatite pellets are suspended in Ecoscint A and radioactivity is assessed using beta scintigraphy. The mean of all triplicate data points (counts per minute, cpm's) is determined. Specific binding is calculated by subtracting nonspecific cpm's (defined as counts that remain following separation of reaction mixture containing recombinant receptor, radioligand, and excess unlabeled ligand) from total bound cpm's (defined as counts that remain following the separation of reaction mixture containing only recombinant receptor, radioligand). Compound potency is determined by means of $IC_{50}$ determinations (the concentration of a compound needed to inhibition 50% of the of the total specific tritiated estradiol bound). Specific binding in the presence of varying concentrations of compound is determined and calculated as percent specific binding of total specific radioligand bound. Data are plotted as percent inhibition by compound (linear scale) versus compound concentration (log scale).

Effect on Total Cholesterol Levels

The effect of the compounds of the present invention on plasma levels of total cholesterol is measured in the following way. Blood samples are collected via cardiac puncture from anesthetized female (S-D) rats 4–6 months of age that are bilaterally ovariectomized and treated with the compound (1–1000 µg/kg/day, for example, sc or orally for 28 days or with vehicle for the same time), or sham operated. The blood is placed in a tube containing 3 µL of 5% EDTA (10 µL EDTA/1 mL of blood). After centrifugation at 2500 rpm for 10 minutes at 20° C. the plasma is removed and stored at −20° C. until assay. The total cholesterol is assayed using a standard enzymatic determination kit from Sigma Diagnostics (Procedure No. 352).

Effect on Obesity

Sprague-Dawley female rats at 10 months of age, weighing approximately 450 grams, are sham-operated (sham) or ovariectomized (OVX) and treated orally with vehicle, 17α ethynyl estradiol at 30 µg/kg/day or a compound of formula I at 10–1000 µg/kg/day for 8 weeks. There are 6 to 7 rats in each sub group. On the last day of the study, body composition of all rats is determined using dual energy x-ray abosorptiometry (Hologic QDR-1000/W) equipped with whole body scan software which shows the proportions of fat body mass and lean body mass.

A decrease in fat body mass indicates that the estrogen agonists of formula I are useful in preventing and treating obesity.

Pharmaceutical chemists will easily recognize that physiologically active compounds which have accessible hydroxy groups are frequently administered in the form of pharmaceutically acceptable esters. The literature concerning such compounds, such as estradiol, provides a great number of instances of such esters. The compounds of this invention are no exception in this respect, and can be effectively administered as an ester, formed on the hydroxy groups, just as one skilled in pharmaceutical chemistry would expect. While the mechanism has not yet been investigated, it is believed that esters are metabolically cleaved in the body, and that the actual drug, which such form is administered, is the hydroxy compound itself. It is possible, as has long been known in pharmaceutical chemistry, to adjust the rate or duration of action of the compound by appropriate choices of ester groups.

Certain ester groups are preferred as constituents of the compounds of this invention. The compounds of formula I may contain ester groups at various portions as defined herein above, where these groups are represented as —COOR$^9$. R$^9$ is $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(chloro or fluoro) methyl.

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid. It is usually preferred to administer a compound of this invention in the form of an acid addition salt, as it is customary in the administration of pharmaceuticals bearing a basic group such as the pyrrolidino ring.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

The dose of a compound of this invention to be administered to a human is rather widely variable and subject to the judgement of the attending physician. It should be noted that it may be necessary to adjust the dose of a compound when it is administered in the form of a salt, such as a laureate, the salt forming moiety of which has an appreciable molecular weight. The general range of effective administration rates of the compounds is from about 0.05 mg/day to about 50 mg/day. A preferred rate range is from about 0.25 mg/day to 25 mg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds of this invention are usually administered as pharmaceutical compositions which are important and novel embodiments of the invention because of the presence of the compounds. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

Any of the compounds may be readily formulated as tablets, capsules and the like; it is preferable to prepare solutions from water-soluble salts, such as the hydrochloride salt.

In general, all of the compositions are prepared according to methods usual in pharmaceutical chemistry.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsifed vehicles which allow it to disperse only slowly in the serum.

The following examples will serve to illustrate, but do not limit, the invention which is defined by the claims.

EXAMPLES

Example 1

Cis-6-phenyl-5-[4-(2-pyrrolidin-1-ylethoxy)phenyl]-5,6,7,8-tetrahydronaphthalen-2-ol

Step A cis-1-{2-[4-(6-Methoxy-2-phenyl-1,2,3,4-tetrahydronaphthalen-1-yl)phenoxy]ethyl}pyrrolidine.

A solution of 1-{2-[4-(6-methoxy-2-phenyl-3,4-dihydronaphthalen-1-yl)phenoxy]ethyl}pyrrolidine hydrochloride (nafoxidene hydrochloride) (1.0 g, 2.16 mmol) in 20 mL of absolute ethanol containing 1.0 g of palladium hydroxide on carbon was hydrogenated at 50 psi at 20° C. for 19 hr. Filtration and evaporation provided 863 mg (93%) of cis-1-{2-[4-(6-methoxy-2-phenyl-1,2,3,4-tetrahydronaphthalen-1-yl)phenoxy]ethyl}pyrrolidine: $^1$H-NMR (CDCl$_3$): δ3.50–3.80 (m, 3H), 3.85 (s, 3H), 4.20–4.40 (m, 3H), 6.80–7.00 (m, 3H); MS 428 (P$^+$+1).

Step B

To a solution of 400 mg (0.94 mmol) of the product from Step A in 25 ml of methylene chloride at 0° C. was added, dropwise with stirring, 4.7 ml (4.7 mmol) of a 1.0 M solution of boron tribromide in methylene chloride. After 3 hours at room temperature, the reaction was poured into 100 ml of rapidly stirring satd aq sodium bicarbonate. The organic layer was separated, dried over sodium sulfate, filtered, and concentrated to afford 287 mg (74% yield) of the title substance as the free base. $^1$H-NMR (CDCl$_3$): δ3.35 (dd, 1H), 4.00 (t, 2H), 4.21 (d, 1H), 6.35 (ABq, 4H). The corresponding hydrochloride salt was prepared by treating a solution of the base with excess 4N HCl in dioxane, followed by evaporation to dryness and ether trituration (MS: 415 [P$^+$+1]).

An alternative method useful for the preparation of Example 1 is described below.

Step A

1-{2-[4-(6-Methoxy-3,4-dihydronaphthalen-1-yl)phenoxy] ethyl}pyrrolidine

A mixture of anhydrous CeCl$_3$ (138 g, 560 mmol) and THF (500 mL) was vigorously stirred for 2 h. In a separate flask, a solution of 1-[2-(4-bromophenoxy)ethyl]pyrrolidine (100 g, 370 mmol) in THF (1000 mL) was cooled to −78° C. and n-BuLi (2.6 M in hexanes, 169 mL, 440 mmol) was slowly added over 20 min. After 15 min, the solution was added to the CeCl$_3$ slurry cooled at −78° C. via cannula and the reaction was stirred for 2 h at −78° C. A solution of 6-methoxy-1-tetralone (65.2 g, 370 mmol) in THF (1000 mL) at −78° C. was added to the arylcerium reagent via cannula. The reaction was allowed to warm slowly to room temperature and was stirred for a total of 16 h. The mixture was filtered through a pad of celite. The filtrate was concentrated in vacuo and 3 N HCl (500 mL) and Et$_2$O (500 mL) were added. After stirring for 15 min, the layers were separated. The aqueous layer was further washed with Et$_2$O (2×). The combined organic layers were dried (MgSO$_4$), filtered, and concentrated to provide 6-methoxy-1-tetralone (22 g). The aqueous layer was basified to pH 12 with 5 N NaOH and 15% aqueous (NH$_4$)$_2$CO$_3$ (1000 mL) was added. The aqueous mixture was extracted with CH$_2$Cl$_2$ (2×). The organic solution was dried (MgSO$_4$), filtered, and concentrated to provide a brown oil. Impurities were distilled off (110–140° C. @ 0.2 mmHg) to yield the product (74 g, 57%). $^1$H NMR (250 MHz, CDCl$_3$): δ7.27 (d, J=8.7 Hz, 2H), 6.92–6.99 (m, 3H), 6.78 (d, J=2.6 Hz, 1H), 6.65 (dd, J=8.6, 2.6 Hz, 1H), 5.92 (t, J=4.7 Hz, 1H), 4.15 (t, J=6.0 Hz, 2H), 3.80 (s, 3H), 2.94 (t, J=6.0 Hz, 2H), 2.81 (t, J=7.6 Hz, 2H), 2.66 (m, 2H), 2.37 (m, 2H), 1.84 (m, 4H).

Step B

1-{2-[4-(2-Bromo-6-methoxy-3,4-dihydronaphthalen-1-yl) phenoxy]ethyl}pyrrolidine Pyridinium bromide perbromide (21.22 g, 60.55 mmol) was added portionwise to a solution of 1-{2-[4-(6-methoxy-3,4-dihydronaphthalen-1-yl)phenoxy]ethyl}pyrrolidine (23 g, 72 mmol) in THF (700 mL). The reaction was stirred for 60 h. The precipitate was filtered through a Celite pad with the aid of THF. The off-white solid was dissolved in CH$_2$Cl$_2$ and MeOH and was filtered away from the Celite. The organic solution was washed with 0.5 N aq HCl followed by satd NaHCO$_3$ (aq). The organic solution was dried (MgSO$_4$), filtered, and concentrated to provide a brown solid (21.5 g, 83%). $^1$H NMR (250 MHz, CDCl$_3$): δ7.14 (d, J=8.7 Hz, 2H), 6.97 (d, J=8.8 Hz, 2H), 6.71 (d, J=2.2 Hz, 1H), 6.55 (m, 2H), 4.17 (t, J=6.0 Hz, 2H), 3.77 (s, 3H), 2.96 (m, 4H), 2.66 (m, 4 H), 1.85 (m, 4H).

Step C

1-{2-[4-(6-Methoxy-2-phenyl-3,4-dihydronaphthalen-1-yl) phenoxy]ethyl}pyrrolidine hydrochloride (Nafoxidene hydrochloride)

To a mixture of 1-{2-[4-(2-bromo-6-methoxy-3,4-dihydronaphthalen-1-yl)phenoxy]ethyl}pyrrolidine (19 g, 44 mmol), phenylboronic acid (7.0 g, 57 mmol), and tetrakis (triphenylphosphonium)palladium (1.75 g, 1.51 mmol) in THF (300 mL) was added Na$_2$CO$_3$ (13 g, 123 mmol) in H$_2$O (100 mL). The reaction was heated at reflux for 18 h. The layers were separated and the organic layer was washed with H$_2$O followed by brine. The organic solution was dried (MgSO$_4$), filtered, and concentrated to yield 17.96 g of a brown solid. The residue was dissolved in a 1:1 mixture of CH$_2$Cl$_2$ and EtOAc (250 mL) and 1 N HCl in Et$_2$O (100 mL) was added. After stirring for 2 h, product was allowed to crystallize from solution and 11 g of material was collected by filtration. Concentration of the mother liquor to half its volume provided an additional 7.3 g of product.

Step D cis-1-{2-[4-(6-Methoxy-2-phenyl-1,2,3,4-tetrahydronaphthalen-1-yl)phenoxy]ethyl}pyrrolidine 1-{2-[4-(6-Methoxy-2-phenyl-3,4-dihydronaphthalen-1-yl)phenoxy]ethyl}pyrrolidine hydrochloride (nafoxidene hydrochloride) (75 g, 162 mmol) was dissolved in 1000 mL of EtOH and 300 mL of MeOH. Dry Pd(OH)$_2$ on carbon was added and the mixture was hydrogenated on a Parr shaker at 50° C. and 50 psi for 68 h. The catalyst was filtered off with the aid of celite and the solvents were removed in vacuo. The resulting white solid was dissolved in CH$_2$Cl$_2$ and the solution was washed with satd NaHCO$_3$ (aq). The organic solution was dried (MgSO$_4$), filtered, and concentrated to yield an off-white solid (62.6 g, 90%).

Step E
cis-6-Phenyl-5-[4-(2-pyrrolidin-1-ylethoxy)phenyl]-5,6,7,8-tetrahydronaphthalene-2-ol A mixture of cis-1-{2-[4-(6-methoxy-2-phenyl-1,2,3,4-tetrahydronaphthalen-1-yl)phenoxy]ethyl}pyrrolidine (12 g, 28 mmol), acetic acid (75 mL), and 48% HBr (75 mL) was heated at 100° C. for 15 h. The solution was cooled and the resulting white precipitate was collected by filtration. The hydrobromide salt (9.6 g, 69%) was dissolved in $CHCl_3$/MeOH and was stirred with satd $NaHCO_3$ (aq). The layers were separated and the aqueous layer was further extracted with $CHCl_3$/MeOH. The combined organic layers were dried ($MgSO_4$), filtered, and concentrated to yield product as an off-white foam. $^1H$ NMR (250 MHz, $CDCl_3$): δ7.04 (m, 3H), 6.74 (m, 2H), 6.63 (d, J=8.3 Hz, 2H), 6.50 (m, 3H), 6.28 (d, J=8.6 Hz, 2H), 4.14 (d, J=4.9 Hz, 1H), 3.94 (t, J=5.3 Hz, 2H), 3.24 (dd, J=12.5, 4.1 Hz, 1H), 2.95 (m, 4H), 2.78 (m, 4H), 2.14 (m, 1H), 1.88 (m, 4H), 1.68 (m, 1H).

Example 2
Trans-6-phenyl-5-[4-(2-pyrrolidin-1-yl-ethoxy)phenyl]-5,6,7,8-tetrahydronaphthalen-2-ol

Step A
To a solution of cis-1-{2-[4-(6-methoxy-2-phenyl-1,2,3,4-tetrahydronaphthalen-1-yl)phenoxy]ethyl}pyrrolidine (500 mg, 1.17 mmol) in 10 ml of dimethyl sulfoxide at 10° C. was added slowly 4.7 ml (11.7 mmol) of 2.5 M n-butyl lithium in hexane. The reaction was allowed to warm to 20° C. and was stirred for 19 hrs. After addition of water and extraction with ether, the organic layers were combined, dried over magnesium sulfate, filtered and concentrated to dryness to yield 363 mg (73%) of the trans-6-methoxydihydronaphthalene. $^1H$-NMR ($CDCl_3$): δ3.45 (m, 2H), 3.82, (s, 3H), 4.06 (d, 1H), 4.45 (m, 2H), 6.80 (d, 2H).

Step B
Using the boron tribromide deprotection procedure described in Example 1 Step B, 363 mg (0.85 mmol) of the product of Step A was converted to 240 mg (68%) of the title compound. $^1H$-NMR ($CDCl_3$): δ4.02 (d, 1H), 4.45 (m, 2H), 7.00 (d, 2H). The corresponding hydrochloride salt was prepared as described in Step B of Example 1 (MS 414 $P^++1$).

Example 3
1-(4'-Pyrrolidinoethoxyphenyl)-2-(4"-hydroxphenyl)-6-hydroxy-1,2,3,4-tetrahydroisoquinoline hydrochloride

Step A
3-Methoxyphenylacet-4'-methoxyanilide

A solution of 20.0 g (0.120 mole) of 3-methoxyphenylacetic acid and 40 ml (65.3 g, 0.549 mole) of thionyl chloride in 100 ml of benzene was heated at reflux for 2 hours and evaporated to dryness to afford the corresponding acid chloride (assume 0.120 mole). The acid chloride was slurried in 50 ml of ether and added to a mixture of 4-methoxyaniline in 100 ml of ether at 0° C. After stirring at 20° C. overnight, the slurry was filtered to afford a solid which was washed with water, 5.5% aq HCl, water, and ether. Subsequent drying over $P_2O_5$ in vacuo for 4 hr. yielded 19.7 g (60%) of the title substance as a white solid. $^1H$-NMR ($CDCl_3$): δ3.70 (s, 2H), 3.77 (s, 3H), 3.81 (s, 3H).

Step B
N-(4-Methoxyphenyl)-2'-(3"-methoxy phenethylamine) hydrochloride

A slurry of 19.6 g (0.072 mol) of the product of Step A and 6.04 g (0.159 mol) of lithium aluminum hydride in 130 ml of ether and 75 ml of dioxane was heated at 35° C. for 48 hrs. Excess sodium sulfite decahydrate was added and the mixture was filtered and washed with 5% aq HCl. The organic layer was dried over anhydrous magnesium sulfate and concentrated to yield 10.84 g of the title substance as the HCl salt (51%). $^1H$-NMR ($CDCl_3$): δ3.15 (m, 2H), 3.42 (m, 2H), 3.71 (s, 3H), 3.74 (s, 3H).

Step C
N-2-(3'-Methoxphenethyl)-4"-benzyloxybenz-4'"-methoxyanilide

To a slurry of 4.83 g (0.164 mol) of the product of Step B and 2.12 g (0.0164 mol) of diisopropylethylamine in 50 ml of ether was added 0.013 mol of 4-benzyloxybenzoyl chloride [prepared from 3.00 g (0.013 mol) of the corresponding benzoic acid and 7.13 g (0.059 mol) of thionyl chloride in 35 ml of benzene] in 50 ml of ether at 20° C. and the reaction was stirred overnight. After decantation from a precipitate, the ether solution was washed with 5% aq HCl, water, brine, dried over magnesium sulfate, filtered and evaporated to dryness to yield 5.58 g of the title substance (73%). $^1H$-NMR ($CDCl_3$): δ3.00 (m, 2H), 3.75 (m, 9H), 4.05 (m, 2H).

Step D
1-(4'-Benzyloxyphenyl)-2-(4"-methoxyphenyl)-6-methoxy-3,4-dihydro isoquinolinium chloride A solution of 1.04 g (2.22 mmol) of the product of step C in 5 ml of phosphorous oxychloride was heated at 100° C. for 2.5 hrs. The reaction was evaporated to dryness and partitioned between ethyl acetate/water. The ethyl acetate layer was dried over anhydrous magnesium sulfate and concentrated to yield 1.03 g of the title substance as an oil (96%). $^1H$-NMR ($CDCl_3$): δ3.46 (t, 2H), 3.80 (s, 3H), 4.00 (s, 3H), 4.55 (t, 2H).

Step E
1-(4'-Benzyloxyphenyl)-2-(4"-methoxyphenyl)-6-methoxy-1,2,3,4-tetrahydroisoquinoline To 1.00 g of the product of Step D (2.07 mmol) in 10 ml of methanol was added 200 mg (5.28 mmol) of sodium borohydride. After stirring 19 hrs at 25° C., the precipitate was collected and dried in vacuo to yield 611 mg (66%) of the title substance as a foam. $^1H$-NMR ($CDCl_3$): δ2.95 (m, 2H), 3.50 (m, 2H), 3.71 (s, 3H), 3.78 (s, 3H), 5.09 (s, 1H).

Step F
1-(4'-Hydroxyphenyl)-2-(4"-methoxyphenyl)-6-methoxy-1,2,3,4-tetrahydroisoquinoline hydrochloride A solution of 611 mg (1.35 mmol) of the product of Step E in 6 ml of conc. aq HCl and 6 ml of dioxane was heated at 90° C. for 5 hrs. The dioxane was removed in vacuo and the aqueous layer diluted with water. The title compound was isolated (155 mg, 29%) as the precipitated hydrochloride salt. $^1H$-NMR ($CDCl_3$): δ3.72 (s, 3H), 3.76 (s, 3H), 5.94 (s, 1H).

Step G
1-(4'-Pyrrolidinoethoxyphenyl)-2-(4"-methoxyphenyl)-6-methoxy-1,2,3,4-tetrahydroisoquinoline To a slurry of 152 mg (0.382 mmol) of the product of Step F in 5 ml of dioxane and 1 ml of DMF was added 152.8 mg (3.82 mmol) of 60% sodium hydride mineral oil dispersion. After stirring at 45° C. for 0.5 hr., 65 mg (0.382 mmol) of 2-chloroethylpyrrolidine hydrochloride was added slowly portionwise and was stirred for 3 hr at 45° C. After addition of water, the reaction was extracted with ethyl acetate. The ethyl acetate layer was dried over anhydrous magnesium sulfate, filtered, and concentrated to yield 203 mg of crude product which was chromatographed on silica gel with chloroform/methanol (99:1) to afford 78 mg (45%) of the title substance. $^1$H-NMR (CDCl$_3$): δ2.85 (m, 2H), 3.72 (s, 3H), 3.79 (s, 3H), 4.00 (t, 2H), 5.50 (s, 1H).

Step H
1-(4'-Pyrrolidinoethoxyphenyl)-2-(4"-hydroxyphenyl)-6-hydroxy-1,2,3,4-tetrahydroiosquinoline hydrochloride To a solution of 75 mg (0.164 mmol) of the product of Step G in 5 ml of methylene chloride at 0° C. was added dropwise 0.82 ml (0.82 mmol) of 1.0 M boron tribromide in methylene chloride. After stirring at 0° C. for 0.5 hr, the reaction was allowed to proceed at 20° C. for 2 hrs. The reaction was poured into ice cold satd aq sodium bicarbonate. The supernatant was filtered off from the gum which was dissolved in methanol, dried over magnesium sulfate, filtered and evaporated to dryness to yield 53 mg (75%) of the title substance as a foam. $^1$H-NMR (CD$_3$OD): δ4.02 (m, 2H), 5.50 (s, 1H), 6.50–7.00 (m, 11H). The hydrochloride salt prepared in the usual manner was a white solid: MS 431 (P$^+$+1).

Example 4

1-(6'-Pyrrolidinoethoxy-3'-pyridyl)-2-(4"-hydroxyphenyl)-6-hydroxy-1,2,3,4-tetrahydroisoquinoline hydrochloride Step A
1-(6'-Chloro-3'-pyridyl)-2-(4"-methoxyphenyl)-6-methoxy-1,2,3,4-tetrahydroisoquinoline Using the procedures described for Example 3 described in step C, substituting 6-chloronicotinoyl chloride for 4-benzyloxybenzoyl chloride, the title compound was obtained.

Step B
1-(6'-Pyrrolidinoethoxy-3'-pyridyl)-2-(4"-methoxyphenyl)-6-methoxy-1,2,3,4-tetrahydroisoquinoline The product of Step A (500 mg, 1.31 mmol) was slurried in 10 ml of toluene and treated with 364 mg (5.52 mmol) of potassium hydroxide, 346 mg (1.31 mmol) of 18-crown-6, and 318 mg (2.76 mmol) of 1-(2-hydroxyethyl)pyrrolidine. After heating at 80° C. for 18 hr, the reaction was cooled, diluted with water, and extracted with ethyl acetate. The combined organic extracts were washed with brine, dried over magnesium sulfate, filtered, and concentrated to dryness to afford 575 mg of a foam Chromatography on silica gel using 97.5% chloroform/methanol (9:1) and 2.5% conc. NH$_4$OH yielded 127 mg (21%) of the title substance. $^1$H-NMR (CDCl$_3$): δ2.50 (m, 4H), 2.90 (m, 4H), 3.42 (m, 2H), 3.72 (s, 3H), 3.79 (s, 3H), 4.39 (t, 2H), 5.05 (s, 1H).

Step C

The product of Step B was deprotected according to the procedure of Example 1 and converted to the hydrochloride salt in the usual manner to afford the title substance. $^1$H-NMR (CDCl$_3$): δ2.55 (m, 2H), 5.45 (s, 1H); MS (P$^+$+1) 432.

Example 5

1-(4-Azabicycloheptanoethoxyphenyl)-2-(4"-hydroxyphenyl)-6-hydroxy-1,2,3,4-tetrahydroisoquinoline hydrochloride Using the procedures of Example 3, substituting in Step C, 4-(2'-azabicyclo[2.2.1]heptanoethoxy)benzoic acid for 4-benzyloxy benzoic acid, followed by the employment of Steps D, E, and H, the title substance was obtained as a white solid. $^1$H-NMR (CDCl$_3$): δ2.95 (m, 3H), 3.90 (s, 1H), 4.15 (t, 3H), 5.42 (s, 1H); MS 457 (P$^+$+1).

Example 6

(−)-cis-6-Phenyl-5-[6-(2-pyrrolidin-1-ylethoxy) pyridin-3-yl]-5,6,7,8-tetrahydronaphthalen-2-ol Step A
5-Bromo-2-(2-pyrrolidin-1-ylethoxy)pyridine A solution of 2,5-dibromopyridine (15.0 g, 63.3 mmol), powdered KOH (6.39 g, 114 mmol), 1-(2-hydroxyethyl) pyrrolidine (14.58 g, 126.6 mmol), and 18-crown-6 (300 mg, 1.14 mmol) in dry toluene (100 mL) was heated to 70° C. for 1 h. The solution was cooled to room temperature and water and EtOAc were added. The organic layer was washed with water and brine. The solution was dried (MgSO$_4$), filtered, and concentrated in vacuo. Short path distillation (153° C. @ 0.1 mmHg) provided the title compound as a colorless oil which solidified upon cooling (14.9 g, 87%). $^1$H NMR (250 MHz, CDCl$_3$): δ8.15 (d, J=2.4 Hz, 1H), 7.65 (dd, J=2.4, 8.4 Hz, 1H), 6.67 (d, J=8.4 Hz, 1H), 4.38 (t, J=5.8 Hz 2H), 2.84 (t, J=5.8 Hz, 2H), 2.62 (m, 4H), 1.82 (m, 4H).

Step B
6-Methoxy-1-[6-(2-pyrrolidin-1-ylethoxy)pyridin-3-yl]-1,2,3,4-tetrahydronaphthalen-1-ol To a solution of 5-Bromo-2-(2-pyrrolidin-1-ylethoxy) pyridine (7.0 g, 26 mmol) in dry THF (50 mL) at −78° C. was added n-BuLi (2.5 M in hexanes, 12.4 mL, 31.0 mmol) dropwise. After 30 min, 6-methoxy-1-tetralone (4.55 g, 25.8 mmol) in dry THF was added. After stirring for 15 min at −78° C., the reaction was allowed to warm to room temperature. After 30 min, the reaction was poured into aq NaHCO$_3$ (satd). The aqueous layer was extracted with EtOAc (2×). The combined organic solutions were dried (MgSO$_4$), filtered, and concentrated. Flash chromatography (CHCl$_3$:MeOH, 95:5) provided the alcohol (4.23 g, 44%) as a white solid. $^1$H NMR (250 MHz, CDCl$_3$): δ8.07 (d, J=2.5 Hz, 1H), 7.49 (dd, J=2.5, 8.7 Hz, 1H), 7.00 (d, J=8.5 Hz, 1H), 6.73 (m, 3H), 4.45 (t, J=5.7 Hz, 2H), 3.79 (s, 3H), 2.92 (t, J=5.7 Hz, 2H), 2.76 (m, 2H), 2.67 (m, 4H), 2.11 (s, 1H), 2.08 (m, 3H), 1.82 (m, 5H).

Step C
5-(2-Bromo-6-methoxy-3,4-dihydronaphthalen-1-yl)-2-(2-pyrrolidin-1-ylethoxy)pyridine Pyridinium bromide perbromide (3.5 g, 12.2 mmol) was added to a solution of 6-methoxy-1-[6-(2-pyrrolidin-1-ylethoxy)pyridin-3-yl]-1,2,3,4-tetrahydronaphthalen-1-ol (3.3 g, 8.9 mmol) in CH$_2$Cl$_2$ (50 mL). The reaction was stirred for 18 h and aqueous NaHCO$_3$ (satd) was added. The aqueous layer was extracted with CH$_2$Cl$_2$ and the combined organic solution was washed with water and brine. The organic solution was dried (MgSO$_4$), filtered, and concentrated. Flash chromatography (CHCl$_3$:MeOH, 95:5) provided the desired vinyl bromide (2.65 g, 70%). $^1$H NMR (250 MHz, CDCl$_3$): δ8.0 (d, J=2.4 Hz, 1H), 7.41 (dd, J=2.4, 8.4 Hz, 1H), 6.83 (d, J=8.4 Hz, 1H), 6.69 (m, 1H), 6.55 (m, 2H), 4.92 (t, J=5.8 Hz, 2H), 3.76 (s, 3H), 2.94 (m, 6H), 2.64 (m, 4 H), 1.82 (m, 4H).

Step D
5-(6-Methoxy-2-phenyl-3,4-dihydronaphthalen-1-yl)-2-(2-pyrrolidin-1-ylethoxy)pyridine Phenyllithium (1.8 M in cyclohexane/ether, 3.8 mL, 7.0 mmol) was added slowly to zinc chloride (0.5 M in THF, 14 mL, 7.0 mmol) at 0° C. After stirring for 15 min, 5-(2-bromo-6-methoxy-3,4-dihydronaphthalen-1-yl)-2-(2-pyrrolidin-1-ylethoxy)pyridine (1.0 g, 2.3 mmol) in dry THF (20 mL) was added followed by Pd(PPh$_3$)$_4$ (200 mg, 0.173 mmol). The reaction was warmed to room temperature and was heated at reflux for 4 h. The reaction was poured into aqueous NH$_4$Cl solution (satd). The aqueous layer was washed with CHCl$_3$ (2×) and the combined organic solutions were washed with water followed by brine. The organic solution was dried (MgSO$_4$), filtered, and concentrated in vacuo. Flash chromatography (CHCl$_3$:MeOH, 95:5) provided the title compound (680 mg, 68%). $^1$H NMR (250 MHz, CDCl$_3$): δ7.78 (d, J=2.1 Hz, 1H), 7.27 (m, 1H), 7.07 (m, 5H), 6.68 (m, 4H), 4.40 (t, J=5.8 Hz, 2H), 3.80 (s, 3H), 2.88 (m, 6H), 2.71 (m, 4 H), 1.81 (m, 4H).

Step E cis-5-(6-Methoxy-2-phenyl-1,2,3,4-tetrahydronaphthalen-1-yl)-2-(2-pyrrolidin-1-ylethoxy)pyridine Pd(OH)$_2$ (20%, 77 mg) was flame dried under vacuum and was added to a solution of 5-(6-methoxy-2-phenyl-3,4-dihydronaphthalen-1-yl)-2-(2-pyrrolidin-1-ylethoxy) pyridine (286.4 mg, 0.6714 mmol) in acetic acid (50 mL). The mixture was hydrogenated on a Parr shaker at 50 psi and at 50° C. for 16 h. The catalyst was filtered off with the aid of celite and the acetic acid was removed in vacuo. $^1$H NMR indicated that the reaction was incomplete and the residue was resubjected to the reaction conditions (50 psi and 60° C.) for an additional 6 h. The catalyst was removed via filtration through celite and the solvent was removed in vacuo. Radial chromatography (solvent gradient, CH$_2$Cl$_2$ to 10% MeOH in CH$_2$Cl$_2$) provided the desired material (207 mg, 72%). $^1$H NMR (250 MHz, CDCl$_3$): δ7.19 (m, 4H), 6.84 (m, 3H), 6.75 (d, J=2.4 Hz, 1H), 6.68 (dd, J=2.4, 8.4 Hz, 1H), 6.59 (dd, J=2.4, 8.4 Hz, 1H), 6.40 (d, J=8.4 Hz, 1H), 4.35 (t, J=5.7 Hz, 2H), 4.21 (d, J=4.8 Hz, 1H), 3.82 (s, 3H), 3.38 (m, 1H), 3.06 (m, 2H), 2.90 (t, J=5.7 Hz, 2H), 2.69 (m, 4H), 2.11 (m, 2H), 1.84 (m, 4H).

Step F cis-6-Phenyl-5-[6-(2-pyrrolidin-1-ylethoxy)pyridin-3-yl]-5,6,7,8-tetrahydronaphthalen-2-ol To a solution of cis-5-(6-methoxy-2-phenyl-1,2,3,4-tetrahydronaphthalen-1-yl)-2-(2-pyrrolidin-1-ylethoxy) pyridine (69.6 mg, 0.162 mmol) in dry CH$_2$Cl$_2$ (3 mL) at 0° C. was added AlCl$_3$ (110 mg, 0.825 mmol) followed by excess EtSH (400 μL). After 0.5 h, the reaction was warmed to room temperature and additional AlCl$_3$ (130 mg) was added. After 0.5 h, aqueous NaHCO$_3$ (satd) was carefully added and the aqueous layer was extracted with CH$_2$Cl$_2$/MeOH (3×). The combined organic layers were dried (MgSO$_4$), filtered, and concentrated. Radial chromatography (solvent gradient, CH$_2$Cl$_2$ to 15% MeOH in CH$_2$Cl$_2$) provided the deprotected material (64.6 mg, 96%) as an off-white solid. $^1$H NMR (250 MHz, CDCl$_3$): δ7.18 (m, 3H), 6.96 (d, J=2.4 Hz, 1H), 6.82 (m, 2H), 6.70 (d, J=2.4Hz, 1H), 6.67 (d, J=8.4Hz, 1H), 6.62 (dd, J=2.4, 8.5 Hz, 1H), 6.52 (dd, J=2.4, 8.4 Hz, 1H), 5.80 (d, J=8.5 Hz, 1H), 4.45 (m, 2H), 4.18 (d, J=4.8 Hz, 1H), 3.40 (m, 1H), 3.04 (m, 3H), 2.75 (m, 6H), 2.11 (m, 1H), 1.88 (m, 4H). The two enantiomers were isolated by chromatography on a 5 cm id×5 cm Chiracel OD column using 5% ethanol/95% heptane with 0.05% diethylamine.

Enantiomer 1: R$_t$=17.96 min, [α]$_d$=+242 (c=1, MeOH);
Enantiomer 2: R$_t$=25.21 min, [α]$_d$=−295 (c=1, MeOH).

Example 7

Cis-6-(4-fluoro-phenyl)-5-[4-(2-piperidin-1-yl-ethoxy)phenyl]-5,6,7,8-tetrahydronaphthalen-2-ol Step A 1 g of 1-[4'-piperidino ethoxy phenyl]-2-[4"-fluoro phenyl]-6-methoxy-3,4-dihydronaphthalene (which can be made as in Example 1 but replacing phenylboronic acid in Step C with 4-fluorophenylboronic acid) in 35 ml acetic acid was added palladium hydroxide on carbon (20%, 1 g)(flame dried in vacuo). The mixture was hydrogenated on a Parr shaker at 50° C. and 50 psi for 4 hours. Filtration through Celite and concentration yielded 1.2 g of crude reaction product which was used without further purification in the next step. $^1$H-NMR (250 MHz, CDCl$_3$): δ1.9 (m), 3.1 (m), 3.25 (m), 3.8 (s, 3H), 4.2 (d, 1H), 4.25 (bd), 6.35 (d, 2H), 6.5 (d, 2H), 6.65 (m), 6.75 (m), 6.8–6.88 (m). m/z 460 (M+1)

Step B

A solution of cis-1-[4'-piperidinoethoxy phenyl]-2-[4"-fluoro phenyl]-6-methoxy-1,2,3,4-tetrahydro naphthalene-1-yl]phenoxy}-ethyl)-piperidine (540 mg, 1.17 mmol) in anhydrous CH$_2$Cl$_2$ was cooled to 0° C. followed by the addition of BBr$_3$[5.8 mL (1 M solution in CH$_2$Cl$_2$), 5.88 mmol] dropwise. The reaction was allowed to warm to room temperature and stirred for another hour. After the reaction was complete, the reaction was cooled back to 0° C. and aqueous NaHCO$_3$ was carefully added. The aqueous layer was extracted with CH$_2$Cl$_2$ (3×). The organic layer was dried over MgSO$_4$, filtered and concentrated. The crude product was radially chromatographed (solvent 4:1 ether/hexane, 1% triethylamine) to provide the deprotected product. The HCl salt product was form with 1M HCl/Ether solution followed by trituration with EtOAc/THF to provide 126 mg of product. $^1$H NMR (250 MHz, CDCl$_3$): δ6.80 (m,4H), 6.63 (m, 4H), 6.50 (dd, 1H), 6.40 (d, 2H), 4.22 (dd, 3H), 3.72 (m, 2H), 3,48 (dd, 2H), 3.0 (bm, 2H), 1.83 (m, 9H). m/z446 (M+1)

Example 8

(−) Cis-6-phenyl-5-[4-(2-pyrrolidin-1-yl-ethoxy) phenyl]-5,6,7,8-tetrahydronaphthalen-2-ol The racemic compound of Example 1 (3 g) was subjected to enantiomeric separation on a 5 cm×5 cm Chiralcell OD column employing 99.95% (5% EtOH/95% heptane)/0.05% diethylamine as the element to afford 1 g of a fast eluting (+) enantiomer and 1 g of a slow (−) eluting enantiomer, both of which possessed identical NMR, MS and TLC behavior as the racemate. Alternatively, a crystallization procedure using R-binap phosphoric acid can be employed to effect resolution. In 20 ml of methanol and 20 ml of methylene chloride was added 7.6 g (0.0184 mol) of the product of Example 1 and 6.4 g (0.0184 mol) of R-(−)-1, 1'-binaphthyl-2,2'-diyl hydrogen phosphate. After solution was complete, evaporation of solvent followed by trituration with ether afforded 14.2 g of racemic salt. This solid was slurried in 500 ml of dioxane and 25 ml of methanol and the resulting mixture was heated until the initial solid dissolved. On standing for 1 hour, a white precipitate formed (6.8 g) which was collected and which HPLC (using the conditions above) indicated to be approximately 73% enantiomerically pure. This material was slurried in 250 ml of absolute ethanol and heated until solution was achieved, at which time the solution was allowed to stand at room temperature overnight. The collected crystals were washed with cold ethanol followed by ether to afford 3.1 g of 98% enantiomerically pure salt; a second crop of 588 mg was also obtained. Partitioning between 1:2 methanol/methylene chloride and 1% aqueous sodium hydroxide afforded the corresponding free base which was converted to the hydrochloride salt (HCl in dioxane). Recrystallization from acetonitrile/methylene chloride afforded the levorotatory preferred enantiomer hydrochloride corresponding to Example 1. [(α$_D$−330.6 (c=0.05, CH$_2$Cl$_2$]; mp 260–263° C.

Example 9

Cis-6-(4'-hydroxyphenyl)-5-[4-(2-piperidin-1-ylethoxy)phenyl]-5,6,7,8-tetrahydronaphthalen-2-ol.

Following the procedures described for the preparation of Example 1, the title compound was obtained. $^1$H NMR (CDCl$_3$): δ3.12 (m, 1H); 3.90 (m, 2H); 4.15 (d, 1H); 6.15–6.72 (m, 11H); FAB MS (M+1) 430.

Example 10

1-(4'-Piperidinoethoxyphenyl)-2-(4''-hydroxyphenyl)-6-hydroxy-1,2,3 4-tetrahydroisoquinoline hydrochloride Using the procedure of Example 3 described in step G, substituting N-2-chloroethylpiperidine hydrochloride for N-2-chloroethylpyrrolidine hydrochloride, the title compound was obtained. $^1$H NMR (CDCl$_3$): δ2.65 (m, 2H); 2.75 (m, 2H); 5.45 (s, 1); 6.50–7.00 (m, 11H); FAB MS(M+1) 445.

Example 11

1-(4'-Pyrrolidinoethoxoxyphenyl)-2-(4''-fluorophenyl)-6-hydroxy-1,2,3,4-tetrahydroisoquinoline hydrochloride The title compound was obtained using the procedure of Example 3 described in step A, substituting 4-fluoroaniline for 4-methoxyaniline. $^1$H NMR (CDCl$_3$): δ2.12 (m, 2H); 3.65 (m, 2H); 4.45 (m, 2H); 6.10 (s, 1H); 7.5 (m, 2H); FAB MS(M+1) 433.

Example 12

1-(4'-Pyrrolidinoethoxyphenyl)-2-phenyl-6-hydroxy-1,2,3,4-tetrahydroisoquinoline hydrochloride The title compound was prepared using the procedure of Example 3 described in step A, substituting aniline for 4-methoxyaniline. $^1$H NMR (CDCl$_3$): δ1.70 (m, 4H); 2.70 (m, 2H); 4.00 (m, 2H); 5.70 (s, 1H); 6.60–7.25 (m, 12H); FAB MS(M+1) 415.

We claim:
1. A compound of the formula:

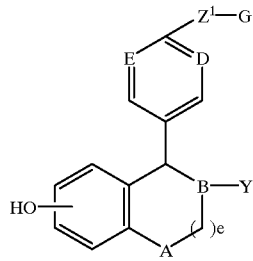

wherein:

A and D represent C;

B and E represent CH and N; with the proviso that B and N can not represent CH simultaneously;

Y is
 (a) phenyl, optionally substituted with 1–3 substituents independently selected from R$^4$;
 (b) naphthyl, optionally substituted with 1–3 substituents independently selected from R$^4$;
 (c) C$_3$–C$_8$ cycloalkyl, optionally substituted with 1–2 substituents independently selected from R$^4$;
 (d) C$_3$–C$_8$ cycloalkenyl, optionally substituted with 1–2 substituents independently selected from R$^4$;
 (e) a five membered heterocycle containing up to two heteroatoms selected from the group consisting of —O—, —NR$^2$— and —S(O)$_n$—, optionally substituted with 1–3 substituents independently selected from R$^4$;
 (f) a six membered heterocycle containing up to two heteroatoms selected from the group consisting of —O—, —NR$^2$— and —S(O)$_n$— optionally substituted with 1–3 substituents independently selected from R$^4$; or
 (g) a bicyclic ring system consisting of a five or six membered heterocyclic ring fused to a phenyl ring, said heterocyclic ring containing up to two heteroatoms selected from the group consisting of —O—, —NR$^2$—, NR$^2$— and —S(O)$_n$—, optionally substituted with 1–3 substituents independently selected from R$^4$;

Z$^1$ is
 (a) —(CH$_2$)$_p$W(CH$_2$)$_q$—;
 (b) —O(CH$_2$)$_p$CR$^5$R$^6$—;
 (c) —O(CH$_2$)$_p$W(CH$_2$)$_q$;
 (d) —OCHR$^2$CHR$^3$—; or
 (e) —SCHR$^2$CHR$^3$—;

G is
 (a) —NR$^7$R$^8$;

(b)
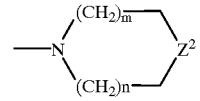

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or
 (c) a bicyclic amine containing five to twelve carbon atoms, either bridged or fused and optionally substituted with 1–3 substituents independently selected from R$^4$;

Z$^1$ and G in combination may be

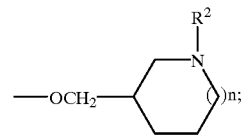

W is
 (a) —CH$_2$—;
 (b) —CH=CH—;
 (c) —O—;
 (d) —NR$^2$—;
 (e) —S(O)$_n$—;

(g) —CR$^2$(OH)—;

(h) —CONR²—;
(i) —NR²CO—;

(j) 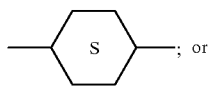; or (k) —C≡C—;

R is hydrogen or $C_1$–$C_6$ alkyl;

$R^2$ and $R^3$ are independently
  (a) hydrogen; or
  (b) $C_1$–$C_4$ alkyl;

$R^4$ is
  (a) hydrogen;
  (b) halogen;
  (c) $C_1$–$C_6$ alkyl;
  (d) $C_1$–$C_4$ alkoxy;
  (e) $C_1$–$C_4$ acyloxy;
  (f) $C_1$–$C_4$ alkylthio;
  (g) $C_1$–$C_4$ alkylsulfinyl;
  (h) $C_1$–$C_4$ alkylsulfonyl;
  (i) hydroxy ($C_1$–$C_4$)alkyl;
  (j) aryl ($C_1$–$C_4$)alkyl;
  (k) —$CO_2$H;
  (l) —CN;
  (m) —CONHOR;
  (n) —$SO_2$NHR;
  (o) —$NH_2$;
  (p) $C_1$–$C_4$ alkylamino;
  (q) $C_1$–$C_4$ dialkylamino;
  (r) —$NHSO_2R$;
  (s) —$NO_2$;
  (t) -aryl; or
  (u) —OH;

$R^5$ and $R^6$ are independently $C_1$–$C_8$ alkyl or together form a $C_3$–$C_{10}$ carbocyclic ring;

$R^7$ and $R^8$ are independently
  (a) phenyl;
  (b) a $C_3$–$C_{10}$ carbocyclic ring, saturated or unsaturated;
  (c) a $C_3$–$C_{10}$ heterocyclic ring containing up to two heteroatoms, selected from —O—, —N— and —S—;
  (d) H;
  (e) $C_1$–$C_6$ alkyl; or
  (f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, esters, and quaternary ammonium salts thereof.

2. A compound of claim 1 which is of formula:

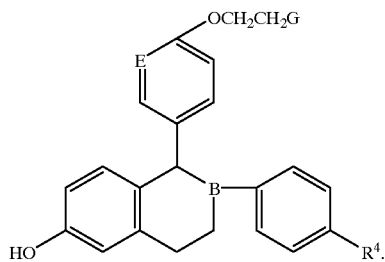

3. A compound of claim 2 wherein G is

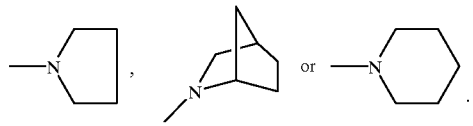

4. A compound of claim 3 wherein $R^4$ is H, OH, F or Cl.

5. A compound of claim 4 wherein:
  B is N; and
  E is CH.

6. A compound of claim 4 wherein:
  B is CH; and
  E is N.

7. The compound of claim 1 which is
  Cis 1-[6'-pyrrolidinoethoxy-3'-pyridyl]-2-phenyl-6-hydroxy-1,2,3,4-tetrahydrohaphthalene.

8. The compound of claim 1 which is
  1-(4'-Pyrrolidinoethoxyphenyl)-2-(4"-fluorophenyl)-6-hydroxy-1,2,3,4-tetrahydroisoquinoline.

9. The compound of claim 1 which is
  1-(4'-Pyrrolidinolethoxyphenyl)-2-phenyl-6-hydroxy-1,2,3,4-tetrahydroisoquinoline.

10. A pharmaceutical composition for treating or preventing osteoporosis comprising a compound of claim 1 and a pharmaceutically acceptable carrier.

11. A pharmaceutical composition for treating or preventing cardiovascular disease or hypercholesterolemia comprising a compound of claim 1 and a pharmaceutically acceptable carrier.

12. A pharmaceutical composition for treating or preventing prostatic disease comprising a compound of claim 1 and a pharmaceutically acceptable carrier.

13. A pharmaceutical composition for lowering serum cholesterol levels comprising a compound of claim 1 and a pharmaceutically acceptable carrier.

14. A pharmaceutical composition for treating or preventing obesity comprising a compound of claim 1 and a pharmaceutically acceptable carrier.

15. A method of treating or preventing osteoporosis in a mammal which comprises administering to a mammal in need of such treatment an effective amount of compound of claim 1.

16. A method of treating or preventing cardiovascular disease or hyperlipidemia in a mammal which comprises administering to a mammal in need of such treatment an effective amount of a compound of claim 1.

17. A method of treating or preventing prostatic disease in a mammal which comprises administering to a mammal in need of such treatment an effective amount of a compound of claim 1.

18. A method of lowering serum cholesterol levels in a mammal which comprises administering to a mammal in need of such treatment an effective amount of a compound of formula I.

19. A method of treating or preventing obesity in a mammal which comprises administering to a mammal in need of such treatment an effective amount of a compound of claim 1.

20. A method of treating or preventing breast cancer in a mammal which comprises administering to a mammal in need of such treatment an effective amount of a compound of claim 1.

21. A method of treating or preventing endometriosis in a mammal which comprises administering to a mammal in need of such treatment an effective amount of a compound of claim 1.

22. A pharmaceutical composition for treating or preventing osteoporosis comprising a compound of claim 1 and a pharmaceutically acceptable carrier.

23. A pharmaceutical composition for treating or preventing breast cancer comprising a compound of claim 1 and a pharmaceutically acceptable carrier.

24. A method of claim 15 wherein said mammal is a male mammal.

25. A method of claim 15 wherein said mammal is a female mammal.

* * * * *